US008440176B2

(12) United States Patent
Laronde et al.

(10) Patent No.: US 8,440,176 B2
(45) Date of Patent: May 14, 2013

(54) COVALENTLY GRAFTED PHARMACEUTICALLY ACTIVE POLYMERS

(75) Inventors: Frank Laronde, Toronto (CA); Fan Gu, Mississauga (CA)

(73) Assignee: Interface Biologics, Inc., Toronto (CA)

( * ) Notice: Subject to any disclaimer, the term of this patent is extended or adjusted under 35 U.S.C. 154(b) by 652 days.

(21) Appl. No.: 12/429,703

(22) Filed: Apr. 24, 2009

(65) Prior Publication Data
US 2010/0034862 A1 Feb. 11, 2010

Related U.S. Application Data

(60) Provisional application No. 61/125,459, filed on Apr. 25, 2008.

(51) Int. Cl.
*A61K 31/00* (2006.01)
(52) U.S. Cl.
USPC ............ 424/78.3; 424/78.17; 424/78.08; 514/772; 514/772.1
(58) Field of Classification Search ............... None
See application file for complete search history.

(56) References Cited

U.S. PATENT DOCUMENTS

| 4,973,493 | A | 11/1990 | Guire |
| 6,770,725 | B2 | 8/2004 | Santerre |
| 2009/0220433 | A1* | 9/2009 | Elmaleh et al. ............ 424/9.35 |

FOREIGN PATENT DOCUMENTS

| CA | 2235907 | 10/1998 |
| EP | 1577670 | 9/2005 |
| WO | WO 2005/110485 | 11/2005 |

OTHER PUBLICATIONS

Grapski et al., "Synthesis and Characterization of Non-Leaching Biocidal Polyurethane," *Biomaterials* 22(16): 2239-2246 (2001).
International Preliminary Report on Patentability (PCT/CA2009/000561), dated Nov. 4, 2010.
International Search Report (PCT/CA2009/000561), dated Jul. 17, 2009.
Written Opinion of the International Searching Authority (PCT/CA2009/000561), dated Aug. 11, 2009.

* cited by examiner

*Primary Examiner* — James Rogers
(74) *Attorney, Agent, or Firm* — Clark & Elbing LLP; Kristina Bicker-Brady

(57) ABSTRACT

The invention relates to graftable polymers comprising biologically active agents and the use of such polymers in the manufacture of shaped articles, such as implantable medical devices and catheters. The graftable polymers are covalently grafted to a surface via one or more grafting moieties incorporated into the pharmaceutically-active graftable polymer. The coated articles of the invention can further comprise tie-coats, and the ratio of polymer:tie coat can be used to adjust the rate of drug elution.

5 Claims, 10 Drawing Sheets

Figure 1: Dependence of Concentration of Silicone Doped Epidel Polyurea/Polyurethane Formulations to Elution of Pharmaceutical in a 1 x 1 cm film format measured by Minimum Inhibitory Concentration against *E. coli* (Polymer 17)

Figure 2: Dependence of Concentration of Silicone Doped Epidel Polyurea/Polyurethane Formulations to Elution of Pharmaceutical in a 1 x 1 cm film format measured by High Performance Liquid Chromatography (Polymer 17)

Figure 3: Dependence of Concentration of Silicone Doped Epidel Polyurethane Formulations to Elution of Pharmaceutical in a 1 x 1 cm film format measured by Minimum Inhibitory Concentration against *E. coli* (Polymer 19)

Figure 4: Dependence of Concentration of Silicone Doped Epidel Polyurethane Formulations to Elution of Pharmaceutical in a 1 x 1 cm film format measured by High Performance Liquid Chromatography (Polymer 19)

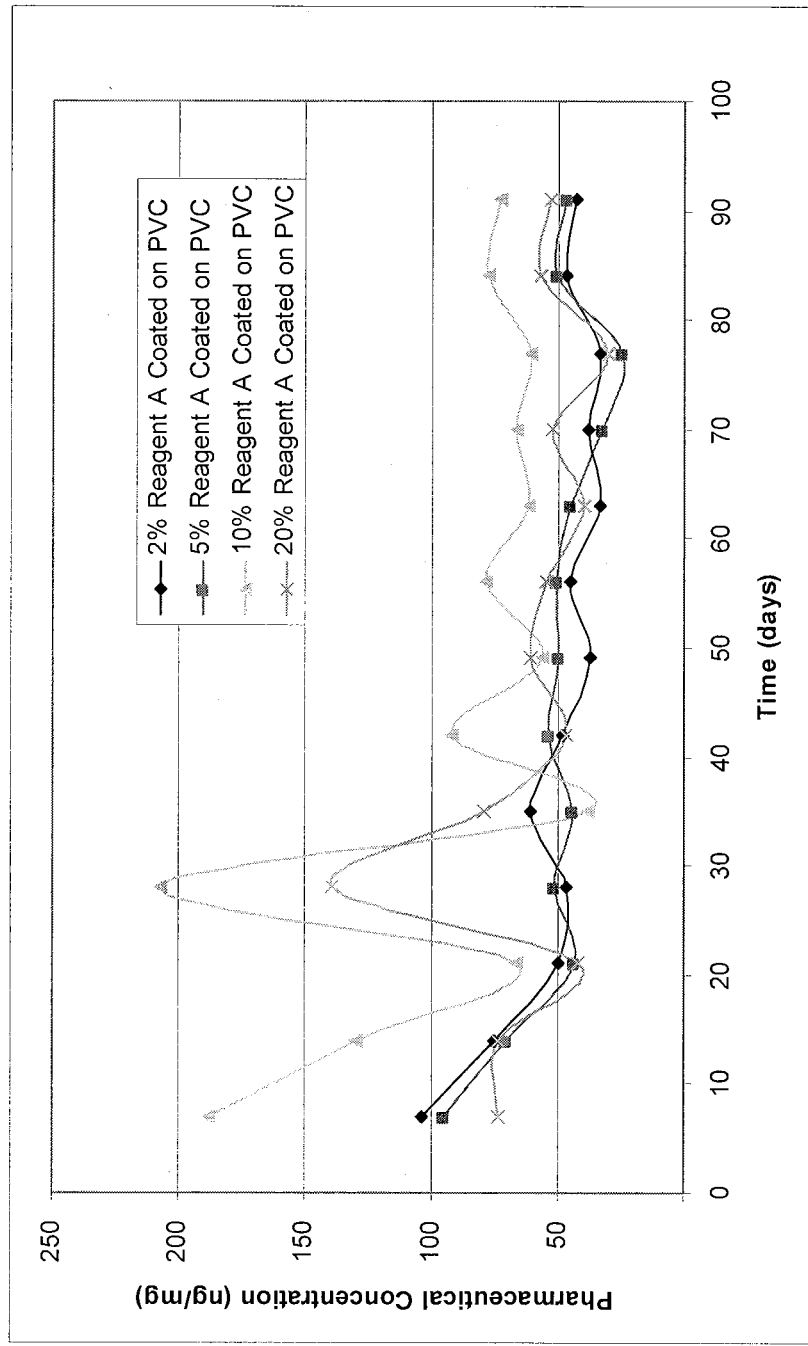
Figure 8: Dependence of base polymer on Elution of Pharmaceutical from a SANPAH Doped Epidel Formulations measured by Minimum High Performance Liquid Chromatography (Polymer 21)

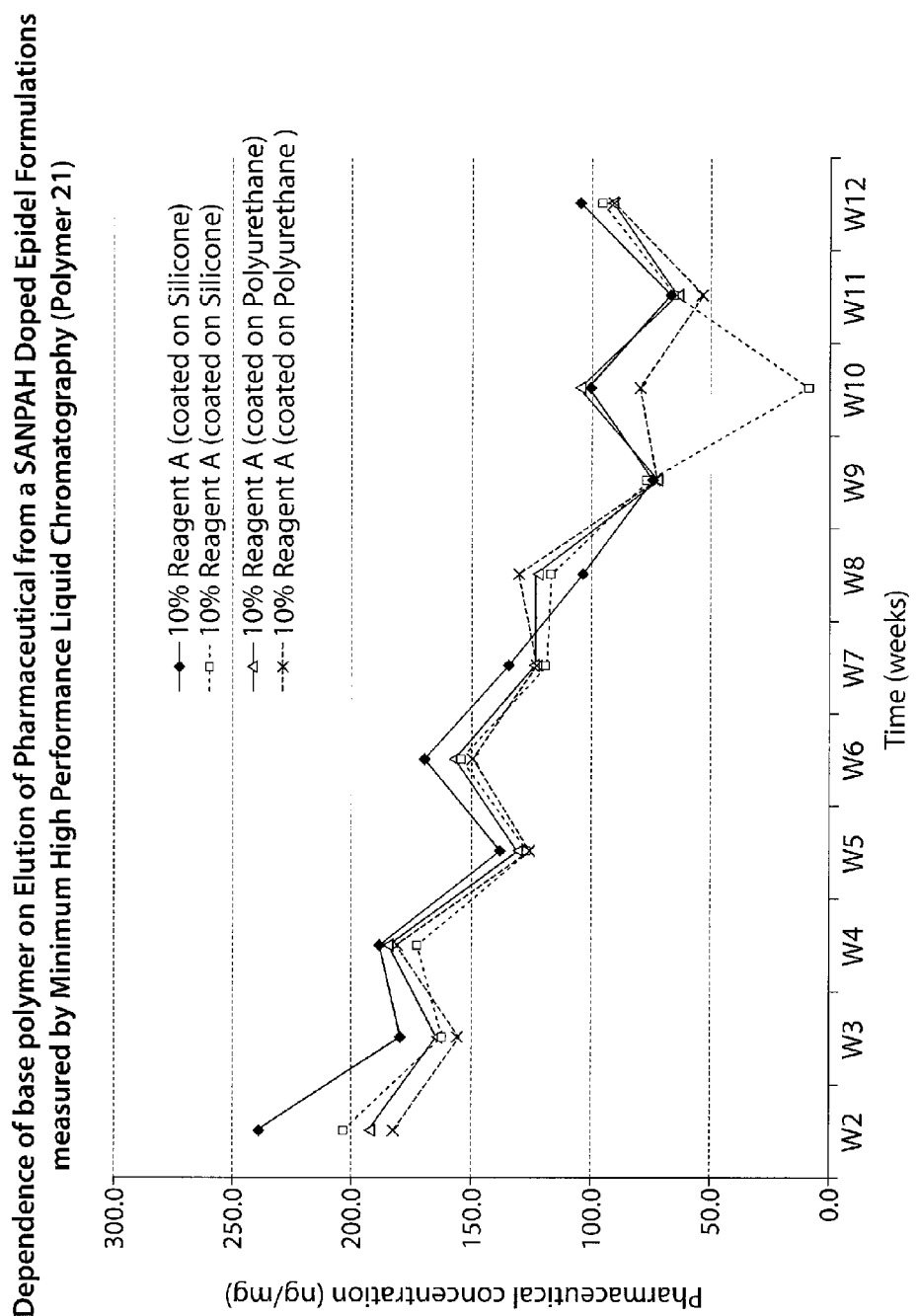

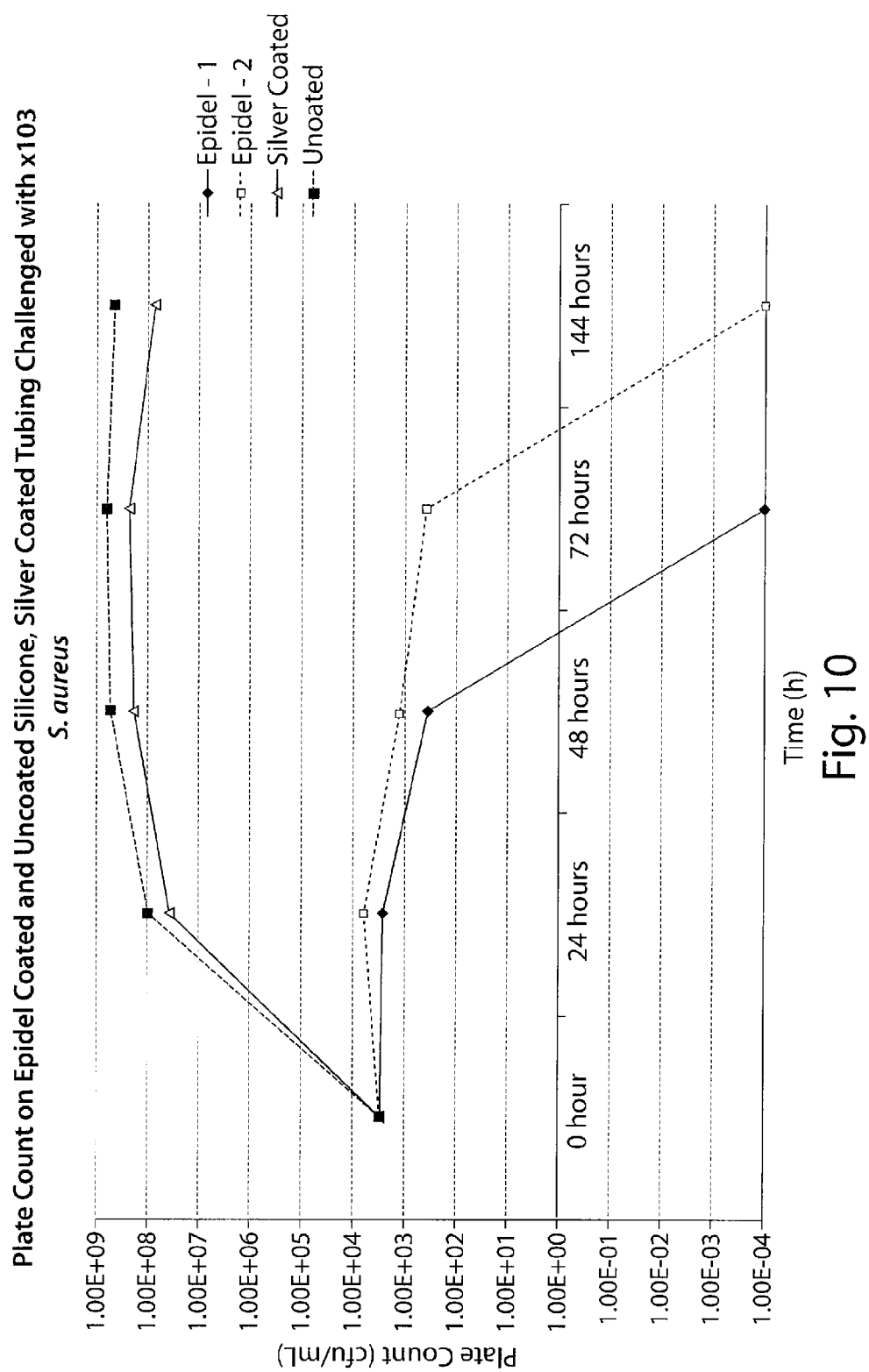

COVALENTLY GRAFTED PHARMACEUTICALLY ACTIVE POLYMERS

CROSS-REFERENCE TO RELATED APPLICATIONS

This application claims benefit from U.S. Provisional Application No. 61/125,459, filed Apr. 25, 2008, hereby incorporated by reference.

BACKGROUND OF THE INVENTION

The invention features graftable polymers including biologically active agents and the use of such polymers in the manufacture of shaped articles.

Polymeric materials have been widely used for manufacturing of medical devices such as artificial organs, implants, medical devices, vascular prostheses, blood pumps, artificial kidney, heart valves, pacemaker lead wire insulation, intra-aortic balloon, artificial hearts, dialyzers and plasma separators, among others. The polymer used within a medical device must be biocompatible (e.g., must not produce toxic, allergic, inflammatory reactions, or other adverse reactions). It is the physical, chemical and biological processes at the interface, between the biological system and the synthetic materials used, which defines the short- and long-term potential applications of a particular device. In general, the exact profile of biocompatibility and biodegradation, including chemical and physical/mechanical properties i.e., elasticity, stress, ductility, toughness, time dependent deformation, strength, fatigue, hardness, wear resistance, and transparency for a biomaterial are extremely variable.

The polymeric coating of a medical device may also serve as a repository for delivery of a biologically active agent. Where the active agent is a pharmaceutical drug, it is often desirable to release the drug from the medical device over an extended period of time. Most systems for kinetically controlled direct drug delivery employ a polymer. For example, the agent may be released as the polymer enzymatically degrades or disintegrates in the body or may diffuse out of the polymeric matrix at a controlled rate. A site-specific drug transfer system can produce a high concentration of agent at the treatment site, while minimizing the adverse effects associated with systemic administration.

In order to maintain the effectiveness of the polymeric coating, non-productive surface degradation or erosion should be minimized such that sufficient quantities of the drug-releasing polymer remain available for the required duration of pharmaceutical activity. One representative pathway of surface erosion is the flaking of the surface of a blended polymer. The use of excess amounts of a pharmaceutically active polymer is one means by which sufficient quantities of drug may be ensured. The administration of excess amount of drug and drug-containing polymer, however, may lead to the release of drug beyond an optimal time frame. Such outcomes may lead to undesirable side effects in patients. In the manufacture of shaped articles using blends of base polymers with polymers that include biologically active agents, reducing the proportion of the base polymer in order to accommodate increased amounts of pharmaceutically active polymers may adversely affect the mechanical properties of the shaped article. As a result, there is a need for pharmaceutically active polymers, polymer surfaces, shaped articles, and implantable medical devices with increased longevity that will maintain pharmaceutical efficacy for the desired time period as well as retain the desirable properties of the base polymer.

SUMMARY OF THE INVENTION

The invention features graftable polymers including biologically active agents and the use of such polymers in the manufacture of shaped articles, such as implantable medical devices and catheters. The graftable polymers are covalently grafted to a surface via one or more grafting moieties incorporated into the pharmaceutically-active graftable polymer. These polymers show pharmaceutical efficacy while reducing possible adverse side effects in patients or mechanical defects in the device that result from high concentrations of the pharmaceutically active agent.

Accordingly, in a first aspect the invention features a graftable polymer including subunits that include one or more biologically active agents; an oligomeric segment; and a grafting moiety capable of forming a covalent bond with a surface, with the graftable polymer having a molecular weight between 14 KDa and 2000 KDa. The molecular weight of any of the graftable polymers of the invention may also be between 14-50 KDa, 14-100 KDa, 14-200 KDa, 25-200 KDa, 50-200 KDa, 50-190 KDa, 50-180 KDa, 50-170 KDa, 50-160 KDa, 50-150 KDa, 50-140 KDa, 50-130 KDa, 50-120 KDa, 50-100 KDa, 50-90 KDa, 50-90 KDa, 50-80 KDa, 50-70 KDa, 50-60 KDa, 14-300 KDa, 14-400 KDa, 14-500 KDa, 14-600 KDa, 14-700 KDa, 14-800 KDa, 14-900 KDa, or 14-1000 KDa.

In certain embodiments, the graftable polymer is described by Formula (I)

$$C1\text{-}[Bio\text{-}(C1\text{-}\{Oligo\text{-}G'\})_o\text{-}]_p \qquad (I)$$

In Formula (I) each Bio is, independently, one or more biologically active agents or precursors thereof; C1 is a coupling segment linking Bio to Oligo; Oligo includes a repeating monomeric unit or units that number less than 50 monomeric units and has a molecular weight less than 5 KDa; G' includes a grafting moiety that is located along the main chain of the graftable polymer; and each of o and p is, independently, an integer greater than 0 but less than 150. Oligo may number less than 50, 45, 40, 35, 30, 25, 20, 15, 10, or even less than 5. Each of o and p may also be any integer between 1-5, 1-10, 1-15, 1-20, 1-25, 1-30, 1-35, 1-40, 1-45, 1-50, 1-55, 1-60, 1-65, 1-70, 1-75, 1-80, 1-85, 1-90, 1-95, 1-100, 1-105, 1-110, 1-115, 1-120, 1-125, 1-130, 1-135, 1-140, 1-145, or 1-150.

In other embodiments, the graftable polymer is described by Formula (II)

$$C1\text{-}[Bio_{\overline{l}}(C1\text{-}Oligo)_o\text{-}]_p \qquad (II)$$
$$\phantom{C1\text{-}[Bio_{\overline{l}}(C1\text{-}Oligo)_o\text{-}]_p}\!\!\!\!G''$$

In Formula (II) each Bio is, independently, one or more biologically active agents or precursors thereof; C1 is a coupling segment linking Bio to Oligo; Oligo includes a repeating monomeric unit or units that number less than 50 monomeric units and has a molecular weight less than 5 KDa; G" includes a grafting moiety that is pendant from the main chain of the graftable polymer; and each of o and p is an integer greater than 0 but less than 150. Oligo may number less than 50, 45, 40, 35, 30, 25, 20, 15, 10, or even 5. Each of o and p may be, independently, any integer between 1-5, 1-10, 1-15, 1-20, 1-25, 1-30, 1-35, 1-40, 1-45, 1-50, 1-55, 1-60, 1-65, 1-70, 1-75, 1-80, 1-85, 1-90, 1-95, 1-100, 1-105, 1-110, 1-115, 1-120, 1-125, 1-130, 1-135, 1-140, 1-145, or 1-150. In certain embodiments, G" is covalently tethered to Bio, C1, or Oligo.

In other embodiments, the graftable polymer is described by Formula (III)

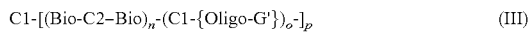

(III)

In Formula (III) each Bio is, independently, one or more biologically active agents or precursors thereof; C1 is a coupling segment linking Bio to Oligo; C2 is a hydrolysable coupling segment or a polyamide linker susceptible to hydrolysis by a peptidase enzyme linking Bio to Bio; Oligo includes a repeating monomeric unit or units that number less than 50 monomeric units and has a molecular weight less than 5 KDa; G' includes a grafting moiety that is located along the main chain of the graftable polymer; and each of n, o, and p is, independently, an integer greater than 0 but less than 150. Oligo may number less than 50, 45, 40, 35, 30, 25, 20, 15, 10, or even less than 5. Each of n, o, and p may also be any integer between 1-5, 1-10, 1-15, 1-20, 1-25, 1-30, 1-35, 1-40, 1-45, 1-50, 1-55, 1-60, 1-65, 1-70, 1-75, 1-80, 1-85, 1-90, 1-95, 1-100, 1-105, 1-110, 1-115, 1-120, 1-125, 1-130, 1-135, 1-140, 1-145, or 1-150.

In still other embodiments, the graftable polymer is described by Formula (IV)

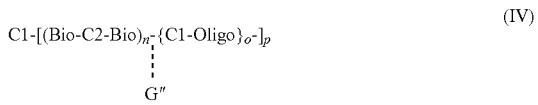

(IV)

In Formula (IV), each Bio is, independently, one or more biologically active agents or precursors thereof; C1 is a coupling segment linking Bio to Oligo; C2 is a hydrolysable coupling segment or a polyamide linker susceptible to hydrolysis by a peptidase enzyme linking Bio to Bio; Oligo includes a repeating monomeric unit or units that number less than 50 monomeric units and has a molecular weight less than 5 KDa; G" includes a grafting moiety that is pendant from the main chain of the graftable polymer; and each of n, o, and p is, independently, an integer greater than 0 and less than 150. Oligo may number less than 50, 45, 40, 35, 30, 25, 20, 15, 10, or even less than 5. Each of n, o, and p may also be any integer between 1-5, 1-10, 1-15, 1-20, 1-25, 1-30, 1-35, 1-40, 1-45, 1-50, 1-55, 1-60, 1-65, 1-70, 1-75, 1-80, 1-85, 1-90, 1-95, 1-100, 1-105, 1-110, 1-115, 1-120, 1-125, 1-130, 1-135, 1-140, 1-145, or 1-150. In certain embodiments, G" is covalently tethered to Bio, C1, C2, or Oligo.

In certain embodiments, the graftable polymer of Formula (II) or (III) includes G', which includes a grafting moiety that includes an electrophile, a nucleophile, a component of a cycloaddition reaction, or a component of a coupling reaction.

Electrophiles that can be used in the polymers and articles of the invention include, without limitation, activated silicon centers. For example, G' can be described by the formula

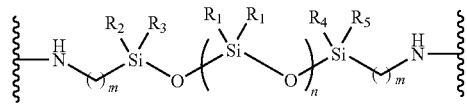

wherein, independently, $R_1$ is selected from —$C_{1-6}$ alkyl or —$OC_{1-6}$ alkyl; each $R_2$, $R_3$, $R_4$, and $R_5$ is —$OC_{1-6}$ alkyl; m is an integer between 1 and 5; and n is an integer greater than 0 and less than 250. In some embodiments, m is 1, 2, 3, 4, or 5 and n is greater than 0 and less than 100, 95, 90, 85, 80, 75, 70, 65, 60, 55, 50, 45, 40, 35, 30, 25, 20, 15, 10, or even less than 5. In some embodiments, $R_1$ is —$CH_3$, —$OCH_3$, or —$OCH_2CH_3$ and $R_2$, $R_3$, $R_4$, and $R_5$ are selected from —$OCH_3$ or —$OCH_2CH_3$. In certain embodiments, $R_1$ is —$OCH_2CH_3$; $R_2$, $R_3$, $R_4$, and $R_5$ are —$OCH_2CH_3$; and m=3.

Alternatively, G' can be described by the formula

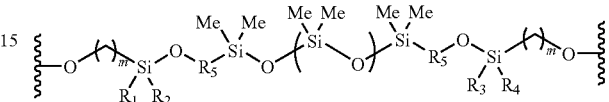

wherein, independently: $R_1$, $R_2$, $R_3$, and $R_4$ are selected from —$OC_{1-6}$ alkyl; $R_5$ is selected from —$(CH_2)_p$— or —$(CH_2)_p$O—; m is an integer between 1-5; n is an integer greater than 0 and less than 250; and p is an integer between 0-6. In some embodiments, m is 1, 2, 3, 4, or 5; n is greater than 0 and less than 100, 95, 90, 85, 80, 75, 70, 65, 60, 55, 50, 45, 40, 35, 30, 25, 20, 15, 10, or even less than 5; and p is 0, 1, 2, 3, 4, 5, or 6. In other embodiments, $R_1$, $R_2$, $R_3$, and $R_4$ are selected from —$OCH_3$ or —$OCH_2CH_3$. In certain embodiments, $R_1$, $R_2$, $R_3$, and $R_4$ are —$OCH_2CH_3$; $R_5$ is —$(CH_2)_2O$—; and m is 1.

In other embodiments, the graftable polymer of Formula (II) or (III) includes G', which includes a grafting moiety that includes a component of a coupling reaction. In still other embodiments, G' includes a grafting moiety that includes a hydridosilane. In certain embodiments, G' is

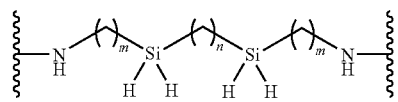

wherein, independently, m and n are integers between 1-6. In some embodiments, each m and n is, independently, 1, 2, 3, 4, 5, or 6. In certain embodiments, m is 3 and n is 1.

In some embodiments, the graftable polymer of any of Formulas (I), (II), (III), and (IV) includes G" which includes a grafting moiety that includes an electrophile, a nucleophile, a component of a cycloaddition reaction, or a component of a coupling reaction.

In other embodiments, G" includes an electrophile or a component of a cycloaddition reaction. In some embodiments, G" is

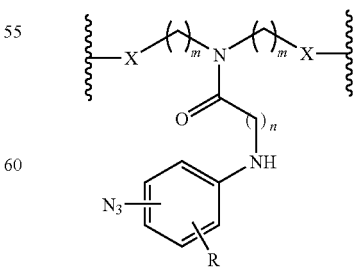

wherein, independently, X is either —NH— or —O—; m is an integer between 1 and 6; n is an integer between 0 and 6;

and R is an optional substituent selected from —H; —NO₂, or —CF₃. In some embodiments, each m is, independently, 1, 2, 3, 4, 5, or 6 and n is 0, 1, 2, 3, 4, 5, or 6. For example, G" can include an electrophile and be selected from

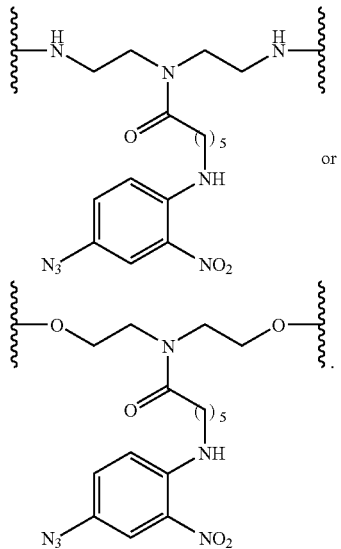

In certain embodiments,
Bio is ciprofloxacin or chlorhexidine;
C1 comprises 2,2,4-trimethylhexamethylene diisocyanate (THDI);
Oligo comprises poly(ε-caprolactone) diol (PCL); and
G" is

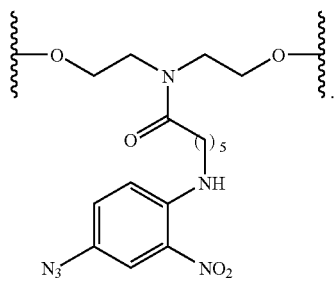

In some embodiments of the invention, the total weight of all G' or G" is 0.5-50% of the molecular weight of the graftable, pharmaceutically active polymer. The total weight of G' or G" relative to the molecular weight of the graftable, pharmaceutically active polymer may also be 0.5-5%, 0.5-10%, 0.5-15%, 0.5-20%, 0.5-25%, 0.5-30%, 0.5-35%, 0.5-40%, 0.5-45%, 1-10%, 1-9%, 1-8%, 1-7%, 1-6%, 1-5%, 1-4%, 1-3%, 1-2%, 2-10%, 2-9%, 2-8%, 2-7%, 2-6%, 2-5%, 2-4%, 2-3%, 3-10%, 3-9%, 3-8%, 3-7%, 3-6%, 3-5%, or 3-4%.

Another aspect of the invention features an article having a surface covalently tethered to a pharmaceutically active polymer and the pharmaceutically active polymer includes subunits that include one or more biologically active agents; an oligomeric segment; and at least one covalent bond to the surface, wherein the pharmaceutically active polymer has a molecular weight between 14 Kda and 2000 Kda. The molecular weight of the pharmaceutically active polymer may also be between 14-50 KDa, 14-100 KDa, 14-200 KDa, 25-200 KDa, 50-200 KDa, 50-190 KDa, 50-180 KDa, 50-170 KDa, 50-160 KDa, 50-150 KDa, 50-140 KDa, 50-130 KDa, 50-120 KDa, 50-100 KDa, 50-90 KDa, 50-90 KDa, 50-80 KDa, 50-70 KDa, 50-60 KDa, 14-300 KDa, 14-400 KDa, 14-500 KDa, 14-600 KDa, 14-700 KDa, 14-800 KDa, 14-900 KDa, or 14-1000 KDa.

In some embodiments, the pharmaceutically active polymer is described by Formula (V)

C1-[Bio-(C1-{Oligo-G'})$_o$-]$_p$    (V)

In Formula (V) each Bio is, independently, one or more biologically active agents or precursors thereof; C1 is a coupling segment linking Bio to Oligo; Oligo includes a repeating monomeric unit or units that number less than 50 monomeric units and with molecular weights less than 5 KDa; G' includes a grafted moiety that is located along the main chain of the pharmaceutically active polymer and covalently tethered to the surface; and each of o and p is, independently, an integer greater than 0 and less than 150. Oligo may number less than 50, 45, 40, 35, 30, 25, 20, 15, 10, or even less than 5. Each of o and p may also be any integer between 1-5, 1-10, 1-15, 1-20, 1-25, 1-30, 1-35, 1-40, 1-45, 1-50, 1-55, 1-60, 1-65, 1-70, 1-75, 1-80, 1-85, 1-90, 1-95, 1-100, 1-105, 1-110, 1-115, 1-120, 1-125, 1-130, 1-135, 1-140, 1-145, or 1-150.

In other embodiments, the pharmaceutically active polymer is described by Formula (VI)

In Formula (VI) each Bio is, independently, one or more biologically active agents or precursors thereof; C1 is a coupling segment linking Bio to Oligo; Oligo includes a repeating monomeric unit or units that number less than 50 monomeric units and with molecular weights less than 5 KDa; G" includes a grafted moiety that is pendant from the main chain of the pharmaceutically active polymer and covalently tethered to the surface; and each of o and p is, independently, an integer greater than 0 and less than 150. Oligo may number less than 50, 45, 40, 35, 30, 25, 20, 15, 10, or even less than 5. Each of o and p may also be, independently, any integer between 1-5, 1-10, 1-15, 1-20, 1-25, 1-30, 1-35, 1-40, 1-45, 1-50, 1-55, 1-60, 1-65, 1-70, 1-75, 1-80, 1-85, 1-90, 1-95, 1-100, 1-105, 1-110, 1-115, 1-120, 1-125, 1-130, 1-135, 1-140, 1-145, or 1-150. In other embodiments, G" is covalently tethered to Bio, C1, or Oligo.

In other embodiments, the pharmaceutically active polymer is described by Formula (VII)

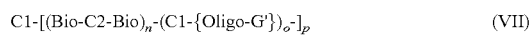

C1-[(Bio-C2-Bio)$_n$-(C1-{Oligo-G'})$_o$-]$_p$    (VII)

In Formula (VII) each Bio is, independently, one or more biologically active agents or precursors thereof; C1 is a coupling segment linking Bio to Oligo; C2 is a hydrolysable coupling segment or a polyamide linker susceptible to hydrolysis by a peptidase enzyme linking Bio to Bio; Oligo includes a repeating monomeric unit or units that number less than 50 monomeric units and with molecular weights less than 5 KDa; G' includes a grafted moiety that is located along the main chain of the pharmaceutically active polymer and covalently tethered to the surface; and each of n, o, and p is independently an integer greater than 0 and less than 150. Oligo may number less than 50, 45, 40, 35, 30, 25, 20, 15, 10, or even less than 5. Each of n, o, and p may also be, independently, any integer between 1-5, 1-10, 1-15, 1-20, 1-25, 1-30, 1-35, 1-40, 1-45, 1-50, 1-55, 1-60, 1-65, 1-70, 1-75, 1-80, 1-85, 1-90, 1-95, 1-100, 1-105, 1-110, 1-115, 1-120, 1-125, 1-130, 1-135, 1-140, 1-145, or 1-150.

In still other embodiments, the pharmaceutically active polymer is described by Formula (VIII)

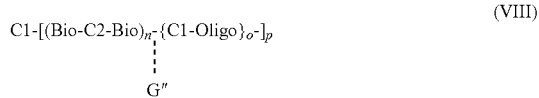
(VIII)

In Formula (VIII) each Bio is, independently, one or more biologically active agents or precursors thereof; C1 is a coupling segment linking Bio to Oligo; C2 is a hydrolysable coupling segment or a polyamide linker susceptible to hydrolysis by a peptidase enzyme linking Bio to Bio; Oligo includes a repeating monomeric unit or units that number less than 50 monomeric units and with molecular weights less than 5 KDa; G″ includes a grafted moiety that is pendant from the main chain of the pharmaceutically active polymer and covalently tethered to the surface; and each of n, o, and p is independently an integer greater than 0 and less than 150. Oligo may number less than 50, 45, 40, 35, 30, 25, 20, 15, 10, or even less than 5. Each of n, o, and p may also be, independently, any integer between 1-5, 1-10, 1-15, 1-20, 1-25, 1-30, 1-35, 1-40, 1-45, 1-50, 1-55, 1-60, 1-65, 1-70, 1-75, 1-80, 1-85, 1-90, 1-95, 1-100, 1-105, 1-110, 1-115, 1-120, 1-125, 1-130, 1-135, 1-140, 1-145, or 1-150. In further embodiments, G″ is covalently tethered to Bio, C1, C2, or Oligo.

In other embodiments, the pharmaceutically active polymer of Formula (VI) or (VII) includes G′ which includes a grafted moiety formed by reaction of an activated silicon center with a nucleophile.

In still other embodiments, G′ is

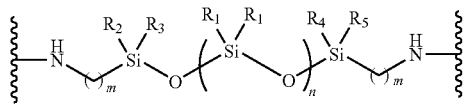

wherein, independently, $R_1$ is selected from $—C_{1-6}$ alkyl or $—OC_{1-6}$ alkyl; each $R_2$, $R_3$, $R_4$, and $R_5$ is $—OC_{1-6}$ alkyl or a covalent bond to the base or base polymer, wherein at least one of $R_2$, $R_3$, $R_4$, or $R_5$ is a covalent bond to the base polymer; m is an integer between 1 and 5; and n is an integer greater than 0 and less than 250. In some embodiments, m is 1, 2, 3, 4, or 5 and n is greater than 0 and less than 250, 225, 200, 175, 150, 125, 100, 75, 50, 25, 10, or even less than 5. In other embodiments, $R_1$ is $—CH_3$, $—OCH_3$, or $—OCH_2CH_3$; and $R_2$, $R_3$, $R_4$, and $R_5$ are selected from $—OCH_3$, $—OCH_2CH_3$, or a covalent bond to the base or base polymer, wherein at least one of $R_2$, $R_3$, $R_4$, or $R_5$ is a covalent bond to the base polymer. In further embodiments, $R_1$ is $—OCH_2CH_3$; $R_2$, $R_3$, $R_4$, and $R_5$ are selected, independently, from $—OCH_3$, $—OCH_2CH_3$, or a covalent bond to the base or base polymer wherein at least one of $R_2$, $R_3$, $R_4$, or $R_5$ is a covalent bond to the base or base polymer; m is 3; and n is an integer greater than 0.

In some embodiments, Bio includes an anti-microbial. In further embodiments, the anti-microbial is ciprofloxacin or chlorhexidine.

In some embodiments, the surface is a base polymer. In some embodiments, the base polymer includes polysilicones, polyurethanes, latex, polyethyleneterephthalate, or polyvinylchloride.

In other embodiments, the base polymer further comprises tie coats (e.g., tert-butyloxy triacetoxysilane, ethyl triacetoxysilane, methyl triacetoxysilane, the tie coats described in Scheme 1 or Table 1, or any combination thereof). In certain embodiments, the tie-coat is applied separately from the graftable or pharmaceutically active polymer. In other embodiments, tie-coat is applied to the surface as part of a mixture comprising the pharmaceutically active polymer or the graftable polymer. In other embodiments, the weight to weight (w/w) ratio of the pharmaceutically active or graftable polymer:tie coat ranges from 1:10 to 50:1 (e.g., the ratio may be 1:2, 1:1, 2:1, 3:1, 4:1, 5:1, 10:1, 15:1, 20:1, 25:1, 30:1, 35:1, 40:1, 45:1, or 50:1). In certain embodiments, the w/w ratio of the pharmaceutically active or graftable polymer:tie coat is 1:2, 1:1, or 2:1. In other embodiments, the w/w ratio of the pharmaceutically active or graftable polymer:tie coat ranges from 1:2 to 50:1. In other embodiments, the w/w ratio of the polymer:tie coat ranges from (A) 1:10 to 1:1 (e.g., 1:9-1:1; 1:8-1:1; 1:7-1:1; 1:6-1:1; 1:5-1:1; 1:4-1:1; 1:3-1:1; or 1:2-1:1);

(B) 1:1-20:1 (e.g., 1:1-2:1; 1:1-3:1; 1:1-4:1; 1:1-5:1; 1:1-6:1; 1:1-7:1; 1:1-8:1; 1:1-9:1; 1:1-10:1; 1-15:1; 1-20:1; 2:1-3:1; 2:1-4:1; 2:1-5:1; 2:1-6:1; 2:1-7:1; 2:1-8:1; 2:1-9:1; 2:1-10:1; 2:1-15:1; 2:1-20:1; 5:1-7.5:1; 5:1-10:1; 5:1-15:1; 5:1-20:1; 10:1-15:1; 10:1-20:1; or 15:1-20:1); or (C) 20:1-50:1 (e.g., 20:1-25:1; 20:1-30:1; 20:1-35:1; 20:1-40:1; 20:1-45:1; 20:1-50:1; 30:1-40:1; 30:1-50:1; or 40:1-50:1).

In some embodiments, the w/w ratio of the polymer:tie coat is used to adjust the rate of elution of the drug (e.g., the w/w ratio of (A) is used to slow the rate of elution of a drug or the w/w ratio of (B) or (C) is used to increase the rate of elution of a drug.

In some embodiments, the surface includes a ceramic. In certain embodiments, the ceramic is titanium dioxide.

In other embodiments, G′ includes

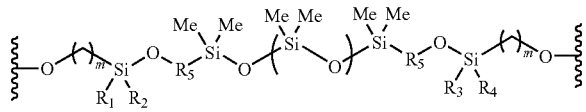

wherein, independently, $R_1$, $R_2$, $R_3$, and $R_4$ are selected from $—OC_{1-6}$ alkyl or a covalent bond to the base or base polymer, wherein at least one of $R_1$, $R_2$, $R_3$, or $R_4$ is a covalent bond to the base or base polymer; $R_5$ is selected from $—(CH_2)_p—$ or $—(CH_2)_pO—$; m is an integer between 1-5; n is an integer greater than 0 and less than 250; and p is an integer between 0-6. In some embodiments, m is 1, 2, 3, 4, or 5; n is greater than 0 and less than 250, 225, 200, 175, 150, 125, 100, 75, 50, 25, 10, or even less than 5; and p is 0, 1, 2, 3, 4, 5, or 6. In other embodiments, $R_1$, $R_2$, $R_3$, and $R_4$ are selected from $—OCH_3$, $—OCH_2CH_3$, or a covalent bond to the base or base polymer wherein at least one of $R_1$, $R_2$, $R_3$, or $R_4$ is a covalent bond to the base or base polymer. In still other embodiments: $R_1$, $R_2$, $R_3$, and $R_4$ are selected, independently, from $—OCH_2CH_3$ or a covalent bond to the base or base polymer wherein at least one of $R_1$, $R_2$, $R_3$, or $R_4$ is a covalent bond to the base or base polymer; $R_5$ is $—(CH_2)_pO—$; m is 1; n is an integer greater than 0 and less than 250; and p is 2.

In some embodiments, Bio includes an anti-microbial. In certain embodiments, the anti-microbial is ciprofloxacin.

In other embodiments, the surface includes a base polymer In certain embodiments, the base polymer includes polysilicones, polyurethanes, latex, polyethyleneterephthalate, or polyvinylchloride. In particular embodiments, the base polymer includes polysilicone.

In other embodiments, the surface includes a ceramic. In certain embodiments, the ceramic is titanium dioxide.

In still other embodiments, the pharmaceutically active polymer of Formulas (V) and (VII) include G' which includes a grafted moiety formed by reaction of a nitrene precursor or a component of a cycloaddition reaction.

In some embodiments, the pharmaceutically active polymer includes the grafted moiety G' that is

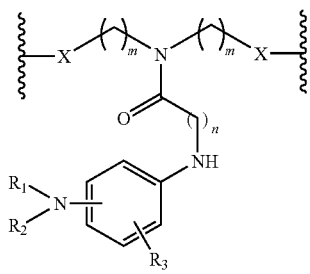

wherein, independently, X is either —NH— or —O—; m is an integer between 1 and 6;

n is an integer between 0 and 6; $R_1$ and $R_2$ are, independently, H or a covalent bond to the base or base polymer, wherein at least one of $R_1$ and $R_2$ is a covalent bond to the base or base polymer; and $R_3$ is an optional substituent selected from —H, —$NO_2$, or —$CF_3$. In certain embodiments, m is 1, 2, 3, 4, 5, or 6 and n is 0, 1, 2, 3, 4, 5, or 6. In further embodiments, X is —O—; m is 2; n is 5; Bio is ciprofloxacin or chlorhexidine; C1 comprises 2,2,4-trimethylhexamethylene diisocyanate (THDI); and Oligo comprises poly($\epsilon$-caprolactone) diol (PCL).

In other embodiments, Bio includes an anti-microbial. In certain embodiments, the anti-microbial is ciprofloxacin.

In some embodiments, the surface includes a base polymer. In certain embodiments, the base polymer includes polysilicones, polyurethanes, latex, polyethyleneterephthalate, or polyvinylchloride. In particular embodiments, the base polymer includes polyurethane or polyvinylchloride.

In still other embodiments, the surface includes a ceramic. In certain embodiments, the ceramic is titanium dioxide.

In some embodiments, the surface the includes a metal or an alloy thereof. In certain embodiments, the metal or alloy thereof is selected from aluminum, cadmium, chromium, cobalt, copper, gold, iridium, iron, magnesium, molybdenum, nickel, palladium, platinum, silver, titanium, zinc, cobalt/chromium alloys, silver alloys, stainless steel, titanium alloys, and pyrolytic carbon.

In some embodiments of the invention, the total weight of all G' or G" is 0.5-50% of the molecular weight of the pharmaceutically active polymer that is covalently grafted to the surface of the article. The total weight of G' or G" relative to the molecular weight of the pharmaceutically active polymer may also be 0.5-5%, 0.5-10%, 0.5-15%, 0.5-20%, 0.5-25%, 0.5-30%, 0.5-35%, 0.5-40%, 0.5-45%, 1-5%, 1-10%, 1-15%, 1-20%, 1-25%, 1-30%, 1-35%, 1-40%, 1-45%, 1-50%, 5-10%, 5-15%, 5-20%, 5-25%, 5-30%, 5-35%, 5-40%, 5-45%, or 5-50%.

In another aspect of the invention, the article of any of the embodiments described herein is an implantable medical device, self-supporting film, or fiber.

In some embodiments, the article is an implantable medical device selected from a cardiac-assist device, a catheter, a stent, a prosthetic implant, a suture, a cuff, a mesh, a hernia patch, a wound dressing, a bandage, an artificial sphincter, and a drug delivery device.

In certain embodiments, the implantable medical device is a catheter.

In still other embodiments, the pharmaceutically active polymer is tethered to an article including a ceramic surface, a polysilicone surface, a polyurethane surface, a latex surface, a metallic surface, or a polyvinylchloride surface.

In some embodiments, the article includes a surface that includes at least two different pharmaceutically active agents. In other embodiments, the two different pharmaceutically active agents are a membrane active biocide and a fluoroquinolone. In certain embodiments, the membrane active biocide is chlorhexidine and the fluoroquinolone is ciprofloxacin.

In any of the polymers or articles described herein, the biologically active agent may be an anti-inflammatory, anti-oxidant, anti-coagulant, anti-microbial, cell receptor ligands, bio-adhesive molecule, pesticide, bactericide, fungicide, fragrance, or dye. In some embodiments, the biologically active agent is an antimicrobial. In certain embodiments, the graftable polymer includes two biologically active agents. In some embodiments, the graftable polymer includes two anti-microbials.

In any of the polymers or articles described herein, the coupling segments C1 and C2 may be selected, independently, from: ethylene glycol, butanediol, hexanediol, hexamethylenediol, 1,5 pentanediol, 2,2-dimethyl-1,3-propanediol, 1,4-cyclohexanediol, 1,4-cyclohexanedimethanol, tri(ethylene glycol), poly(ethylene glycol), poly(ethylene oxide)diamine, lysine esters, siliconediols and -diamines, polyetherdiols and -diamines, carbonatediols and -diamines, dihydroxy vinyl derivatives, dihydroxy diphenylsulfone, ethylenediamine, hexamethylenediamine, 1,2-diamino-2-methylpropane, 3,3-diamino-N-methyldipropylamine, 1,4 diaminobutane, 1,7-diaminoheptane, or 1,8-diaminooctane.

In any of the polymers or articles of the invention, Oligo may number less than 50, 45, 40, 35, 30, 25, 20, 15, 10, or less than 5 repeating monomeric units and may have a molecular weight of less than 5 KDa, 4.5 KDa, 4 KDa, 3.5 KDa, 3 KDa, 2.5 KDa, 2 KDa, 1.5 KDa, 1 KDa, or even less than 0.5 KDa. Useful repeating monomeric units include polyurethanes, polyureas, polyamides, polyalkylene oxides, polycarbonates, polyesters, polylactones, polysilicones, polyethersulfones, polyolefins, polyvinyls, polypeptides, polysaccharides, or any combination thereof.

Anti-microbial agents useful in any of the polymers or articles of the invention include: penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmatozole, cefotaxime, ceftizoxime, ceftriaxone, cefoperazone, ceftazidime, cefixime, cefpodoxime, ceftibuten, cefdinir, cefpirome, cefepime, chlorhexidine, BAL5788, BAL9141, imipenem, ertapenem, meropenem, astreonam, clavulanate, sulbactam, tazobactam, streptomycin, neomycin, kanamycin, paromycin, gentamicin, tobramycin, amikacin, netilmicin, spectinomycin, sisomicin, dibekalin, isepamicin, tetracycline, chlortetracycline, demeclocycline, minocycline, oxytetracycline, methacycline, doxycycline, erythromycin, azithromycin, clarithromycin, telithromycin, ABT-773, lincomycin, clindamycin, vancomycin, oritavancin, dalbavancin, teicoplanin, quinupristin and dalfopristin, sulphanilamide, para-aminobenzoic acid, sulfadiazine, sulfisoxazole, sulfamethoxazole, sulfathalidine, linezolid, nalidixic acid, oxolinic acid, norfloxacin, perfloxacin, enoxacin, ofloxacin, ciprofloxacin, temafloxacin, lomefloxacin, fleroxacin, grepafloxacin, sparfloxacin, trovafloxacin, clinafloxacin, gatifloxacin, moxifloxacin, gemifloxacin, sitafloxacin, metronidazole, daptomycin, garenoxacin, ramoplanin, faropenem, polymyxin, tigecycline, AZD2563, and trimethoprim.

By "activated carbonyl" is meant a functional group $R^1R^2—C(O)R^3$ or $R^1—R^2C(O)R^3$ wherein, independently, $R^1$ is a bond or an attachment to the graftable monomer, graftable polymer, or surface; $R^2$ is selected from H, optionally substituted $C_{1-12}$ alkyl, optionally substituted arenes, optionally substituted $C_{1-12}$ alkarenes, optionally substituted heteroarenes, or optionally substituted $C_{1-12}$ alkheteroarenes; and $R^3$ is a $C_{1-6}$ alkoxy group, OH, or halide.

By "activated phosphorus center" is meant a grafting moiety that includes a trivalent phosphorus (III) or a pentavalent phosphorus (V) center wherein at least one of the substituents is a $C_1$-$C_6$ alkoxy group. Desirably, the alkoxy group is —$OCH_3$ or —$OCH_2CH_3$.

By "activated silicon center" is meant a grafting moiety that includes a tetrasubstituted silicon center wherein at least one of the substituents is a $C_1$-$C_6$ alkoxy group. Desirably, the alkoxy group is —$OCH_3$ or —$OCH_2CH_3$.

By "activated sulfur center" is meant a grafting moiety that includes a tetravalent sulfur wherein at least one of the substituents is a $C_1$-$C_6$ alkoxy group. Desirably, the alkoxy group is —$OCH_3$ or —$OCH_2CH_3$.

By "alkoxy" is meant a group having the structure —OR, where R is an optionally substituted alkyl group as described herein.

By "allyl" is meant a functional group that is an optionally substituted straight chain or branched chain saturated hydrocarbon group having 1 to 12 carbons, unless otherwise specified. For example, a "$C_{1-10}$ alkyl group" refers to alkyl groups ranging from 1-10 carbons.

By "alkylamino group" is meant a functional group having the structure $R^1R_2NH$ wherein $R^1$ is a bond or an attachment to the graftable monomer, graftable polymer, or surface and $R_2$ is an optionally substituted $C_{1-2}$ alkyl group.

By "alkarene" is meant is a functional group having the structure $R^1—R_2—Ar$ where wherein $R^1$ is a bond or an attachment to the graftable monomer, graftable polymer, or surface, $R_2$ is an optionally substituted $C_{1-8}$ alkyl group, and Ar is an arene.

By "alkheteroarene" is meant is a functional group having the structure $R^1—R_2$-Het where wherein $R^1$ is a bond or an attachment to the graftable monomer, graftable polymer, or surface, $R_2$ is an optionally substituted $C_{1-8}$ alkyl group, and Het is a heteroarene.

By "alkene" is meant a functional group having the structure $R^1R^2C=CR^3R^4$ wherein at least one of $R_1$, $R_2$, $R_3$, or $R_4$ is a bond or an attachment to the graftable monomer, graftable polymer, or a surface $R^1$, $R^2$, $R^3$, or $R^4$ may be selected, independently, from H, optionally substituted $C_{1-12}$ alkyl, optionally substituted arenes, or optionally substituted heteroarenes. Preferred alkenes are those in which $R^1$ is an attachment to the graftable monomer and $R^2$, $R^3$, or $R^4$ are H or $C_{1-3}$ alkyl.

By "alkyl halide" is meant a functional group $R^1R^2CHR^3—X$ wherein, independently, $R^1$ is a bond or an attachment to the graftable monomer, graftable polymer, or surface; $R^2$ is substituted $C_n$ alkyl where n=0-12; and $R^3$ is selected from H, optionally substituted $C_{1-12}$ alkyl, optionally substituted arenes, optionally substituted $C_{1-12}$ alkarenes, optionally substituted heteroarenes, or optionally substituted $C_{1-12}$ alkheteroarene; and X is a halogen.

By "alkyl psuedohalide" is meant a functional group $R^1R^2CHR^3—X$ wherein, independently, $R^1$ is a bond or an attachment to the graftable monomer, graftable polymer, or surface; R is substituted $C_n$ alkyl where n=0-12; and $R^3$ is selected from H, optionally substituted $C_{1-12}$ alkyl, optionally substituted arenes, optionally substituted $C_{1-12}$ alkarenes, optionally substituted heteroarenes, or optionally substituted $C_{1-2}$ alkheteroarene; and X is a pseudohalide.

By "alkyne" is meant a functional group having the structure $R^1R^2C\equiv CR^2$ wherein $R^1$ is a bond or an attachment to the graftable monomer, graftable polymer, or surface and $R^2$ is selected from H, optionally substituted $C_{1-12}$ alkyl, optionally substituted arenes, or optionally substituted heteroarenes. Preferred alkynes are those in which $R^2$ is H, optionally substituted $C_{1-12}$ alkyl, or an optionally substituted arene.

By "amino group" is meant a functional group having the structure $R^1—NH_2$ wherein $R^1$ is a bond or an attachment to the graftable monomer, graftable polymer, or surface.

By "amount sufficient" is meant the amount of biologically active agent necessary to achieve a desired result. The amount sufficient will vary depending upon a variety of parameters, including the condition being treated (e.g., pain or microbial growth, among others), the site being treated, the biologically active agent selected, and the delivery vehicle employed (e.g., implanted device, cream, or pellet, among others). A sufficient amount can be determined for any given set of conditions using standard methods. For example, the release of biologically active agent from a surface can be monitored as a function of the parameters above. Based upon these results, a vehicle prepared which releases the agent at a rate that produces the desired effect.

By "anilido group" is meant a functional group having the structure $R^1R^2NH$ or $R^1$-$R^2$—$NH_2$ wherein $R^1$ is a bond or an attachment to the graftable monomer, graftable polymer, or surface and $R^2$ is an optionally substituted arene.

By "arene" is meant is an optionally substituted $C_6$-$C_{14}$ cyclic hydrocarbon with $[4n+2]\pi$ electrons in conjugation and where n is 1, 2, or 3. Non-limiting examples of arenes include benzene, naphthalene, anthracene, and phenanthrene.

By "azide" is meant a functional group that includes at least one —$N_3$ functional group.

By "base polymer" is meant a polymer having a tensile strength of from about 350 to about 10,000 psi, elongation at break from about 300% to about 1500%, an unsupported thickness of from about 5 to about 100 microns, and a supported thickness of from about 1 to about 100 microns. Base polymers may be selected from: polysilicones (also known as polysiloxanes), polyurethanes, latex that is naturally occurring or synthetic, polysulfones, polycarbonates, polysaccharides, polyesters, polyorthoesters, polyalkylenes, polyethylene, polypropylene, polystyrene, poly(acrylonitrile-butadienestyrene), polybutadiene, polyisoprene, styrenebutadiene-styrene block copolymers, styrene-isoprenestyrene block copolymers, poly-R-methylpentene, polyisobutylene, polymethyl-methacrylate, polyvinylacetate-polyacrylonitrile, polyvinylchloride, polyalkylene terephthalates, polyethyleneterephthalate (also known as Dacron), polyalkyleneoxides, cellulose and its esters and derivatives, polyamides, polyester-polyethers, styrene-isoprenes, styrenebutadienes, thermoplastic polyolefins, styrene-saturated olefins, polyester-polyester, ethylene-vinyl acetate ethylene-ethyl acrylate, ionomers, and thermoplastic polydienes, or mixtures or blends thereof. Preferred base polymers are polysilicones, polyurethanes, latex, polyethyleneterephthalate, and polyvinylchloride, or mixtures or blends thereof.

By "biologically active agent" is meant a molecule that can be coupled to a polyamide linker via a hydrolysable covalent bond. The biologically active agent is selected for some specific and intended physical, pharmacological, or biological action. Typically the biologically active agent has a molecular weight ranging from 40 to 2,000 Da. Biologically active agents that can be used in the methods and compositions of the invention include, without limitation, anti-inflammatory, anti-oxidant, anti-coagulant, anti-microbial (i.e. fluoroquinolones), cell receptor ligands, and bio-adhesive molecules (e.g., oligosaccharides, oligonucleic acid sequences for DNA and gene sequence bonding, and phospholipid head groups to provide cell membrane mimics). Desirably, the biologically active agent is a compound useful for the therapeutic treatment of a plant or animal when delivered to a site of diseased tissue. Alternatively, the biologically active agent can be selected to impart non-therapeutic functionality to a surface. Such agents include, for example, pesticides, bactericides, fungicides, fragrances, and dyes.

By "carbene" is meant a functional group that is a divalent carbon species having six valence electrons and the structure $R^1R^2C$ or $R^1\text{-}R^2CR^3$ wherein $R^1$ is a bond or an attachment to the graftable monomer, graftable polymer, or surface; $R^2$ and $R^3$ are, independently, selected from H, optionally substituted $C_{1-12}$ alkyl, optionally substituted arenes, optionally substituted $C_{1-12}$ alkarenes or optionally substituted carbonyl; and C is a carbon with two electrons that are not part of a covalent bond. The two electrons may be paired (e.g. singlet carbene) or unpaired (e.g. triplet carbene).

By "catalyst" is meant a chemical or biological reagent that is used in a substoichiometric quantity that accelerates the rate of a reaction without being consumed. The use of a catalyst can also result in improved chemical yields from a reaction. Types of catalysts that are useful in the synthesis or the grafting of graftable polymers include, but are not limited to enzymes, RNA, DNA, Lewis acid catalysts, and Lewis basic catalysts that are known in the art. Heterogeneous and homogeneous catalysis may both be useful.

By "ceramics" is meant a material selected from metal oxides or phosphates that include $Ca_5(PO_4)_3(OH)$ (hydroxyapatite), $TiO_2$, $Al_2O_3$, $ZrO_2$ (zirconia), $SiO_2$, or ZnO, or any composite thereof. The ceramic may further include mineral acids such as hydrochloric acid, sulfuric acid, nitric acid.

By "component of a coupling reaction" is meant one of the components that engage in a coupling reaction that include either the σ bond or the π bond that engages in the coupling reaction. Components of coupling reactions include hydridosilanes, alkenes, and alkynes.

By "component of a cycloaddition reaction" is meant one of the components that engage in a cycloaddition reaction. In cycloaddition reactions in which bond formation involves $[4n+2]\pi$ electrons where n is 1, one component will provide $2\pi$ electrons and another component will provide $4\pi$ electrons. Representative components of cycloaddition reactions that provide $2\pi$ electrons include alkenes and alkynes. Representative components of cycloaddition reactions that provide $4\pi$ electrons include 1,3-dienes, α,β-unsaturated carbonyls, and azides.

By "coupling reaction" is meant a reaction including two components in which one component includes a nonpolar σ bond such as Si—H or C—H and the second component includes a π bond such as an alkene or an alkyne that results in either the net addition of the σ bond across the π bond to form C—H, Si—C, or C—C bonds or the formation of a single covalent bond between the two components. A preferential coupling reaction is the addition of Si—H across an alkene (also known as hydrosilylation). Other coupling reactions include Stille coupling, Suzuki coupling, Sonogashira coupling, Hiyama coupling, and the Heck reaction. Catalysts may be used to promote the coupling reaction. Preferential catalysts are those which include Pt(0), Pt(II), or Pt(IV).

By "coupling segment" is meant a molecule or chemical bond covalently linking segments together in the graftable polymer. Typically, coupling segments can have molecular weights ranging from 16 to 2000 Da and have multi-functionality, but preferably di-functionality, to permit coupling of two segments. The coupling segments can be synthesized from the groups of precursor monomers selected from diols, diamines and/or a compounds containing both amine and hydroxyl groups. Precursors that can be incorporated into coupling segments include, without limitation, ethylene glycol, butanediol, hexanediol, hexamethylenediol, 1,5 pentanediol, 2,2-dimethyl-1,3-propanediol, 1,4-cyclohexanediol, 1,4-cyclohexanedimethanol, tri(ethylene glycol), poly(ethylene glycol), poly(ethylene oxide)diamine, lysine esters, siliconediols and -diamines, polyetherdiols and -diamines, carbonatediols and -diamines, dihydroxy vinyl derivatives, dihydroxy diphenylsulfone, ethylenediamine, hexamethylenediamine, 1,2-diamino-2-methylpropane, 3,3-diamino-N-methyldipropylamine, 1,4 diaminobutane, 1,7-diaminoheptane, or 1,8-diaminooctane.

By "cycloaddition reaction" is meant a reaction including two components in which $[4n+2]\pi$ electrons are involved in bond formation when there is either no activation, activation by a chemical catalyst, or activation using thermal energy and n is 1, 2, or 3. A cycloaddition reaction may also be a reaction including two components in which $[4n]\pi$ electrons are involved, there is photochemical activation, and n is 1, 2, or 3. Desirably, $[4n+2]\pi$ electrons are involved in bond formation and n=1. Representative cycloaddition reactions include the reaction of an alkene with a 1,3-diene (Diels-Alder reaction), the reaction of an alkene with an α,β-unsaturated carbonyl (hetero Diels-Alder reaction), and the reaction of an alkyne with an azide (Hüisgen cycloaddition).

By "electrophile" or "electrophilic group" is meant a functional group that engages in the formation of a covalent bond by accepting electrons or it may refer to a functional group that is a precursor to an electrophile. Electrophiles may be selected from nitrenes; nitrene precursors such as azides; carbenes; carbene precursors; activated silicon centers; activated carbonyls; alkyl halides; alkyl pseudohalides; epoxides; electron-deficient arenes; activated phosphorus centers; and activated sulfur centers. Preferential electrophiles are nitrenes, nitrene precursors, and activated silicon centers.

By "epoxide" is meant an optionally substituted three-membered heterocycle consisting of two optionally substituted carbons and one oxygen.

By "fluoroquinolone" is meant a class of antibiotics which exert their antibacterial effects by inhibiting bacterial DNA gyrase and which include a fluorinated quinolone ring system. Fluoroquinolone which can be used in the polymers and articles of the invention include, without limitation, those described in patent publications BE870576; DE3142854; EP047005; EP206283; BE887574; EP221463; EP140116; EP131839; EP154780; EP078362; EP310849; EP520240; and U.S. Pat. Nos. 4,448,962; 4,499,091; 4,704,459; 4,795,751; 4,668,784; and 5,532,239, each of which is incorporated herein by reference. Exemplary fluoroquinolones which can be used in the polymers and articles of the invention include, without limitation, ciprofloxacin (commercially available as Cipro®), enrofloxacin (commercially available as Baytril®), enoxacin (commercially available as Penetrex®, gatifloxacin (commercially available as Tequin®), gemifloxacin (commercially available as Factive®), levofloxacin (commercially available as Levaquin®), lomefloxacin (commercially available as Maxaquin®), moxifloxacin (commercially available as Avelox®), norfloxacin (commercially available as Noroxin®), ofloxacin (commercially available as Floxin®), sparfloxacin (commercially available as Zagam®), trovafloxacin (commercially available as Trovan®), difloxacin, cinofloxacin, pefloxacin, tosufloxacin, temafloxacin, fleroxacin, amifloxacin, binfloxacin, danofloxacin, marbofloxacin, ruflocaxin, and sarafloxacin.

By "graftable polymer" is meant a pharmaceutically active polymer that includes a grafting moiety.

By "grafting" is meant the covalent attachment of a graftable polymer to a surface (e.g., the surface of a base polymer, a ceramic surface, or a metal surface) through the formation of covalent bonds between the graftable polymer and the surface. Covalent attachment may occur, for example, through the formation of C—H, C—C, C—N, C—O, C—S, C—Si, Si—H, Si—N, Si—O, Si—S, Si—Si, N—H bonds, C-metal bonds, N-metal bonds, Si-metal bonds, O-metal bonds, or any combination thereof. For example, grafting can occur through the formation of Si—O, Si—C, or C—N bonds. Covalent attachment can result from combining the two entities, but may also employ an additional activation step in order to promote the reaction. Methods of activation may be selected from chemical treatment of the graftable polymer, chemical treatment of the surface, photolytic activation, thermolytic activation, use of a catalyst, use of stoichiometric or superstoichiometric quantities of a promoter, by other means known in the art, or by any combination of the methods listed. Preferential methods of activation are the chemical treatment of the surface, photolytic activation, and the use of a catalyst.

By "grafting moiety" or "graftable moiety" is meant a functional group capable of forming covalent bonds to a surface by acting as a nucleophile, electrophile, a component in a cycloaddition reaction, or a component in a coupling reaction as described herein to allow grafting.

By "grafted moiety" is meant a segment of a pharmaceutically active polymer that includes a functional group that is covalently tethered to a surface by grafting.

By "halide," "halogen," "hal," or "halo" is meant —F, —Cl, —Br, or —I.

By "heteroarene" is meant an optionally substituted cyclic moiety formed with 5-18 atoms selected from C, S, N, and O and having $[4n+2]\pi$ electrons in conjugation where n=1-3 wherein at least one atom forming the ring is S, N, or O, Non-limiting examples of heteroarenes include furan, benzofuran, isobenzofuran, thiophene, benzothiophene, pyrrole, indoles, pyrazoles, imidazole, benzimidazole, triazoles, benzotriazoles, thiazoles, benzothiazoles, oxazoles, benzoxazoles, oxadiazoles, thiadiazoles, pyridines, pyrimidines, pyrazines, triazines, purines, phthalzine, quinolines, isoquinolines, and quinazolines.

By "hydridosilane" is meant a grafting moiety that includes a tetrasubstituted silicon center wherein at least one of the substituents is a hydrogen.

By "hydroxy group" or "hydroxyl group" is meant a functional group having the structure $R^1$—OH wherein $R^1$ is a bond or an attachment to the graftable monomer, graftable polymer, or surface.

By "metal" or "metallic surface" is meant a material comprising at least one of the metallic elements of Groups 2-14 in the Periodic Table, or any alloy thereof, or any surface oxide thereof. Exemplary metals are: aluminum, cadmium, chromium, cobalt, copper, gold, iridium, iron, magnesium, molybdenum, nickel, palladium, platinum, silver, titanium, and zinc. Exemplary alloys are: cobalt/chromium alloys; silver alloys; stainless steel, such as stainless steel 316; and titanium alloys, such as nickel/titanium alloys (e.g. Nitinol). Other exemplary metallics include pyrolytic carbon.

By "nitrene" is meant a functional group that is a monovalent nitrogen species having six valence electrons and the structure $R^1N$ or $R^1$-$R^2$—N wherein $R^1$ is an attachment to the graftable monomer, graftable polymer, or surface; $R^2$ is selected from optionally substituted $C_{1-12}$ alkyl, optionally substituted arenes, optionally substituted $C_{1-12}$ alkarenes, or optionally substituted carbonyl; and N is a nitrogen with four electrons, at least two of which are paired. The two remaining electrons may be paired (i.e. singlet nitrene) or unpaired (i.e. triplet nitrene).

By "nonpolar a bond" is meant a covalent bond between two elements having electronegativity values, as measured according to the Pauling scale, that differ by less than or equal to 1.0 units. Non-limiting examples of nonpolar a bonds include C—H, Si—H, Si—C, C—Cl, C—Br, C—I, C—B, and C—Sn bonds.

By "nucleophile" or "nucleophilic functional group" is meant an optionally substituted functional group that engages in the formation of a covalent bond by donating electrons from electron pairs or π bonds. In describing grafting moieties that include nucleophiles, it is understood that the functional group will have at least one bond to the graftable monomer, graftable polymer, or a surface. Nucleophiles may be selected from alkenes, alkynes, arenes, heteroarenes, hydroxy groups, phenoxy groups, amino groups, alkylamino groups, anilido groups, thio groups, and thiophenoxy groups. Preferential nucleophiles are hydroxy groups and alkenes.

By "oligomeric segment" or "Oligo" is meant a unit included of a relatively short length of a repeating unit or units, generally less than about 50 monomeric units and molecular weights less than 10,000 but preferably <5000. Preferably, the oligomeric segment is selected from the group consisting of polyurethanes, polyureas, polyamides, polyalkylene oxides, polycarbonates, polyesters, polylactones, polysilicones, polyethersulfones, polyolefins, polyvinyls, polypeptides, polysaccharides; and ether and amine linked segments thereof. Preferred oligomeric segments are polyurethanes.

By "pharmaceutically active polymer" is meant a polymer that includes a biologically active agent and a grafting moiety as described above.

By "phenoxy group" or "phenoxyl group" is meant a functional group having the structure $R^1$-$R^2$—OH wherein $R^1$ is a bond or an attachment to the graftable monomer, graftable polymer, or surface and $R^2$ is an optionally substituted arene.

By "photolytic activation" or "photolysis" is meant the promotion or initiation of a chemical reaction by irradiation of the reaction with light. The wavelengths of light suitable for photolytic activation range between 200-500 nm and include wavelengths that range from 200-260 nm and 300-460 nm. Other useful ranges include 200-230 nm, 200-250 nm, 200-275 nm, 200-300 nm, 200-330 nm, 200-350 nm, 200-375 nm, 200-400 nm, 200-430 nm, 200-450 nm, 200-475 nm, 300-330 nm, 300-350 nm, 300-375 nm, 300-400 nm, 300-430 nm, 300-450 nm, 300-475 nm, and 300-500 nm.

By "chemical treatment" is meant the combination or admixture of the graftable polymer or the surface with a chemical or a solution of a chemical. Chemical that may be used in such processes are: inorganic acids such as HCl, $H_2SO_4$, $HNO_3$, $H_3PO_4$, or any mixture thereof; organic acids such as acetic acid; and organosilane reagents such as trimethylsilyl chloride, acteoxysilanes, alkyoxysilanes. The organosilane reagents are also known as "tie-coats."

By "prodrug" is meant a precursor to a biologically active agent that is converted in vivo, e.g., by enzymatic and/or hydrolytic mechanisms, into a biologically active agent. Prodrugs include, without limitation, esterified biologically active agents.

By "promoter" is meant a reagent used in a stoichiometric or superstoichiometetric quantity that can accelerate the rate of a reaction or improve chemical yields of a reaction. Examples of promoters include N,N-dimethylaminopyridine (DMAP) for nucleophilic additions, carboxylic acid activators such as dicyclohexylcarbodiimide (DCC) and peptide coupling reagents known in the art.

Bond formation in this manner requires that the graftable polymer and/or the surface include a grafting moiety, such as a nucleophile, electrophile, a component of a cycloaddition reaction, a component of a coupling reaction, or a component of a radical recombination reaction. For example, where the graftable polymer includes a nucleophile, the surface is designed to include an electrophile.

By "pseudohalide" is meant a polyatomic functional group having the structure selected from: $-OSO_2C_nF_{(2n+1)}$ where n=1-9; $-OSO_2R^1$ where $R^1$ is optionally substituted $C_{1-6}$ alkyl or optionally substituted arene; or $-OSO_3R^1$, where $R^1$ is optionally substituted $C_{1-6}$ alkyl or optionally substituted arene.

By "thermal activation," "thermolytic activation," or "thermolysis" is meant the promotion or initiation of a chemical reaction by the application of heat to the system. Thermal activation occurs at temperatures above 25-30° C. (ambient temperature) and useful reaction temperatures range from 40-800° C. Other useful temperature ranges for thermolysis include 40-100° C., 40-200° C., 40-300° C., 40-400° C., 40-500° C., 40-600° C., 40-700° C., 100-200° C., 100-300° C., 100-400° C., 100-500° C., 100-600° C., 100-700° C., 100-800° C., 200-300° C., 200-400° C., 200-500° C., 200-600° C., 200-700° C., 200-800° C., 300-400° C., 300-500° C., 300-600° C., 300-700° C., and 300-800° C. The reaction may be carried out under atmospheric pressure but the use of reduced pressure (i.e. vacuum conditions) may also be useful in thermolytic activation. When reduced pressure is used during thermolysis, useful pressures range from $1\times10^{-8}$-$1\times10^2$ torr. Other useful pressure ranges include: $1\times10^{-8}$-1 torr; $1\times10^{-8}$-$1\times10^{-2}$ torr; $1\times10^{-8}$-$1\times10^{-4}$ torr; $1\times10^{-8}$-$1\times10^{-6}$ torr; $1\times10^{-6}$-$1\times10^2$ torr; $1\times10^{-6}$-1 torr; $1\times10^{-6}$-$1\times10^{-2}$ torr; $1\times10^{-6}$-$1\times10^{-4}$ torr; $1\times10^{-4}$-$1\times10^2$ torr; $1\times10^{-4}$-1 torr; $1\times10^{-4}$-$1\times10^{-2}$ torr; $1\times10^{-2}$-$1\times10^2$ torr; and $1\times10^{-2}$-1 torr.

By "thio group" or "thiol group" is meant a functional group having the structure $R^1SH$ wherein R" is a bond or an attachment to the graftable monomer, graftable polymer, or surface.

By "thiophenoxy group" or "thiophenoxyl group" is meant a functional group having the structure $R^1$-$R^2$—SH wherein $R^1$ is a bond or an attachment to the graftable monomer, graftable polymer, or surface and $R^2$ is an optionally substituted arene.

Where a group is described as "optionally substituted," the optional substituents may be selected, independently, from H; $C_{1-10}$ alkyl; $C_{1-10}$ perfluorinated alkyl; halo; $-N_3$, $-NO_2$; $-CN$; $-COR^4$ wherein $R^4$ is selected, independently, from $-H$, $-OH$, $-C_{1-10}$ alkyl, $-C_{1-10}$ alkoxy, -halo, $-N_3$, or $-NR^5R^6$; $-NR^5R^6$, wherein $R^5$ and $R^6$ are selected, independently, from $-H$, -aryl, -alkaryl, -heteroaryl, -alkheteroaryl, $-C_{1-10}$ alkyl, $-C_{1-10}$ alkoxy, or $-COR^4$; -aryl; -alkaryl; -heteroaryl; -alkheteroaryl; $-SR^7$, wherein $R^7$ is selected from $-H$, $-C_{1-10}$ alkyl, -aryl, -alkaryl, -heteroaryl, -alkheteroaryl, or $-C_{10}$ alkyl; $-OR^8$ wherein $R^8$ is selected from $-H$, -aryl, -alkaryl, -heteroaryl, -alkheteroaryl, $-C_{1-10}$ alkyl, $-C_{1-10}$ perfluorinated alkyl, or $-COR^4$; $-SOR^9$ wherein $R^9$ is selected from $-H$, -aryl, -alkaryl, -heteroaryl, -alkheteroaryl, $-OH$, $-C_{1-10}$ alkyl, $-C_{1-10}$ alkoxy, or $-C_{1-10}$ perfluorinated alkyl; and $-SO_2R^{10}$, wherein $R^{10}$ is selected from $-H$, -aryl, -alkaryl, -heteroaryl, -alkheteroaryl, $-OH$, $-C_{1-10}$ alkyl, $-C_{1-10}$ alkoxy, or $-C_{1-10}$ perfluorinated alkyl. A substituted group may have, for example, 1, 2, 3, 4, 5, 6, 7, 8, 9, or 10 substituents as defined herein. A substituent group may itself be further substituted.

Other features and advantages of the invention will be apparent from the following Detailed Description, the drawings, and the claims.

BRIEF DESCRIPTION OF THE DRAWINGS

FIG. 8 shows the release of Ciprofloxacin as measured by HPLC by Polymer 21 (depicted in Scheme 6 and as prepared in Example 7) when grafted to polyvinylchloride (PVC) surfaces according to the procedure of Example 13.

FIG. 9 shows the release of Ciprofloxacin as measured by HPLC by Polymer 21 (depicted in Scheme 6 and as prepared in Example 7) when grafted to silicone and polyurethane surfaces according to the procedure of Example 13.

FIG. 10 shows the effect on the plate count of *S. aureus* using silicone tubing coated with a mixture of ciprofloxacin-containing polymers and tie-coats, silver-coated tubing, and uncoated tubing as described in Example 19.

DETAILED DESCRIPTION

Figure 1:
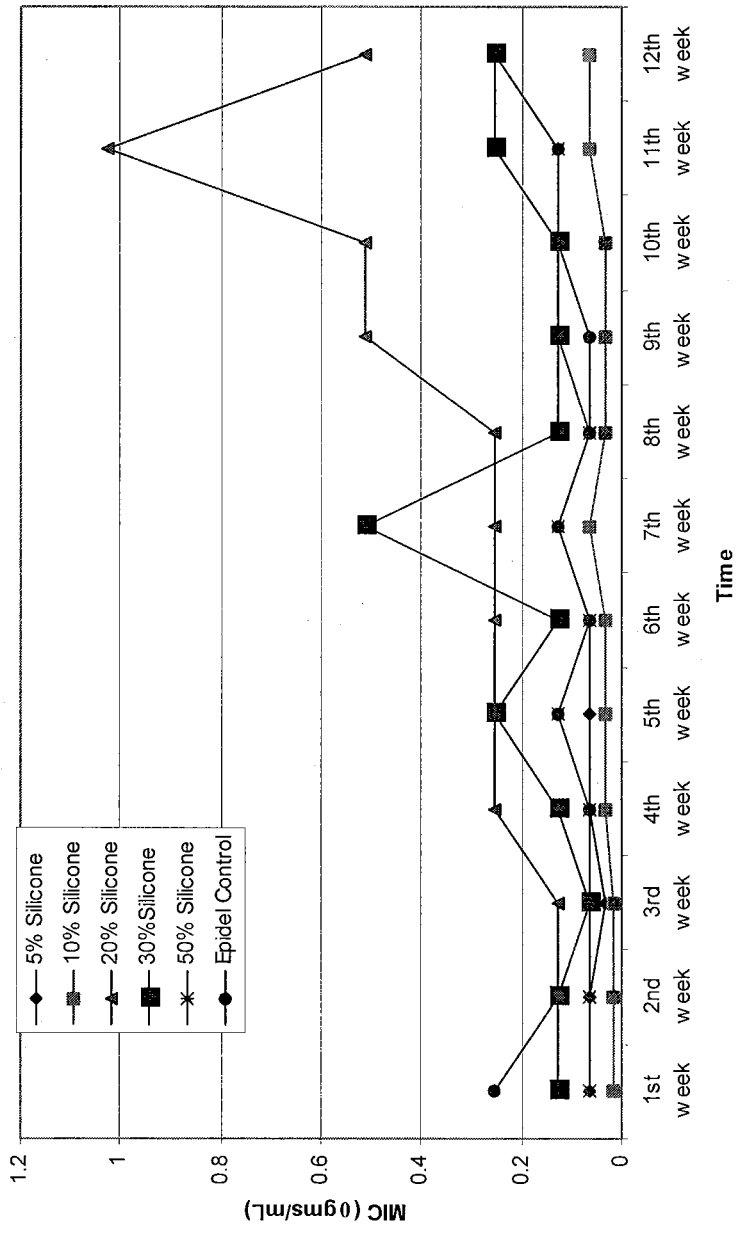
FIG. 1 shows the minimum inhibitory concentration (MIC) measured against an *Escherichia coli* (*E. coli*) clinical strain for pharmaceutical released from Polymer 17 (depicted in Scheme 5 and as prepared in Example 5).

The invention features graftable polymers including biologically active agents and the use of such polymers in the manufacture of shaped articles, such as implantable medical devices and catheters. The graftable polymers are covalently grafted to a surface via one or more grafting moieties incorporated into the pharmaceutically-active graftable polymer. The surfaces that can be modified using the graftable polymers of the invention include, for example, polysilicone base polymers, latex base polymers, polyvinylchloride base polymers, ceramic surfaces, and metallic surfaces. These pharmaceutically active polymers can allow for the manufacture of shaped articles and implantable medical devices with increased longevity that will maintain pharmaceutical efficacy for the desired time period as well as retain the desirable properties of the base polymer.

Grafting Moieties

The graftable, pharmaceutically-active polymers of the invention feature a grafting moiety that can form covalent bonds with a surface. The graftable moiety may be found along the main chain of the polymer or may be pendant from the main chain. Representative, non-limiting grafting moieties include: nucleophiles, electrophiles, components of a cycloaddition reaction, or components of a coupling reaction. The graftable moiety of the polymer can then react with complementary functionality on the surface. For example, where the graftable polymer includes a nucleophile, the surface is designed to include an electrophile.

Nucleophile/Electrophile Reactions

Nucleophiles and electrophiles can engage in bond forming reactions selected from, without limitation, insertion by an electrophile into a C—H bond, insertion by an electrophile into an O—H bond, insertion by an electrophile into an N—H bond, addition of the electrophile across an alkene, addition of the electrophile across an alkyne, addition to electrophilic carbonyl centers, substitution at electrophilic carbonyl centers, addition to ketenes, nucleophilic addition to isocyanates, nucleophilic addition to isothiocyanates, nucleophilic substitution at activated silicon centers, nucleophilic displacement of an alkyl halide, nucleophilic displacement at an alkyl pseudohalide, nucleophilic addition/elimination at an activated carbonyl, 1,4-conjugate addition of a nucleophile to an α,β-unsaturated carbonyl, nucleophilic ring opening of an epoxide, nucleophilic aromatic substitution of an electron deficient arene, a nucleophilic addition to activated phosphorus centers, nucleophilic substitution at activated phosphorous centers, nucleophilic addition to activated sulfur centers, and nucleophilic substitution at activated sulfur centers.

Nucleophiles

The graftable moiety may be selected from optionally substituted alkenes, optionally substituted alkynes, optionally substituted arenes, optionally substituted heteroarenes, hydroxy groups, amino groups, alkylamino groups, anilido groups, and thio groups.

Electrophiles

The graftable moiety may be selected from nitrenes, nitrene precursors such as azides, carbenes, carbene precursors, activated silicon centers, activated carbonyls, anhydrides, isocyanates, thioisocyanates, succinimidyl esters, sulfosuccinimidyl esters, maleimides, alkyl halides, alkyl pseudohalides, epoxides, electron-deficient arenes, activated phosphorus centers, and activated sulfur centers. Examples of polysiloxanes that include activated silicon centers as an electrophilic grafting moiety and that are suitable for use in the graftable polymers of the invention are compounds (1)-(4).

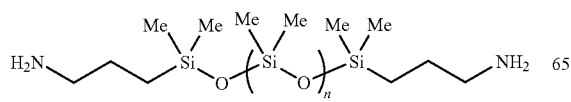

(1)

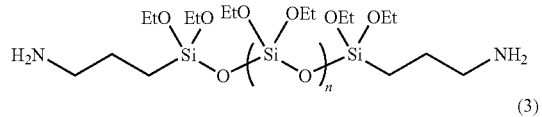

(2)

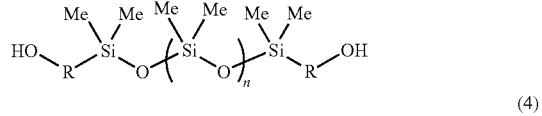

(3)

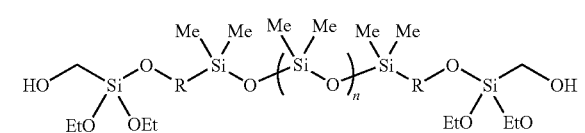

(4)

Alternatively, the pharmaceutically active polymer may include a graftable moiety that requires photolytic or thermolytic activation for grafting to a polymer surface. Graftable moieties that include azide functionality are one example. The azide functional groups are UV labile and, upon photolysis, can lead to the formation of nitrene electrophiles. Alternatively, the heating of these azide compounds can also result in nitrene formation. Two photolytically active segment suitable for use in the graftable pharmaceutically active polymers of the invention include compounds (5) and (6).

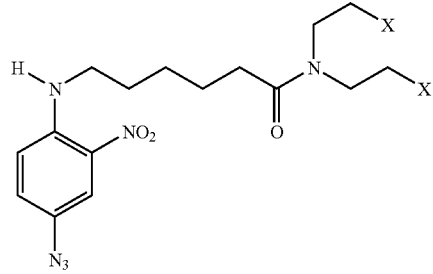

(5) X = NH$_2$
(6) X = OH

Components of Coupling Reactions

Coupling reactions can be used to form covalent bonds between the graftable polymers of the invention and surfaces. Coupling reactions can include but are not limited to: hydrosilylation, Stille coupling, Suzuki coupling, Sonogashira coupling, Hiyama coupling, and the Heck reaction. Selected, non-limiting examples of graftable moieties that include components of coupling reactions are hydridosilanes, alkenes, and alkynes. An exemplary graftable moiety that includes hydridosilane functional groups and that is suitable for use in the graftable pharmaceutically active polymers of the invention is compound (7).

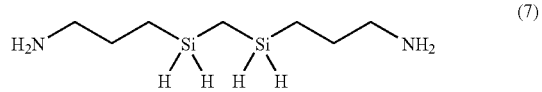 [SMILES: NCCC[SiH2]C[SiH2]CCCN]

(7)

Components of Cycloaddition Reactions.

Cycloadditon reactions can be used to form covalent bonds between the graftable polymers of the invention and surfaces.

Representative cycloaddition reactions include the reaction of an alkene with a 1,3-diene (Diels-Alder reaction), the reaction of an alkene with an α,β-unsaturated carbonyl (hetero Diels-Alder reaction), and the reaction of an alkyne with an azide (Hüisgen cycloaddition). Selected, non-limiting examples of graftable moieties that include components of cycloaddition reactions are: alkenes, alkynes, 1,3-dienes, α,β-unsaturated carbonyls, and azides.

Surfaces

The graftable, pharmaceutically-active polymers of the invention can be grafted to a surface, such as a ceramic surface, metallic surface, or the surface of a base polymer. Exemplary reactions that can lead to the formation of covalent bonds between the graftable polymers of the invention and surfaces include electrophile/nucleophile reactions, coupling reactions, photolysis of UV-labile graftable moieties, and thermolysis of nitrene precursors.

Base Polymers

Examples of base polymers to which the graftable, pharmaceutically-active polymer may be grafted include, but are not limited to, polysilicones (also known as polysiloxanes), polyurethanes, latex that is naturally occurring or synthetic, polysulfones, polycarbonates, polysaccharides, polyesters, polyorthoesters, polyalkylenes, polyethylene, polypropylene, polystyrene, poly(acrylonitrile-butadienestyrene), polybutadiene, polyisoprene, styrenebutadiene-styrene block copolymers, styrene-isoprenestyrene block copolymers, poly-R-methylpentene, polyisobutylene, polymethyl-methacrylate, polyvinylacetate-polyacrylonitrile, polyvinyl chloride, polyalkylene terephthalates, polyethyleneterephthalate (also known as Dacron), polyalkyleneoxides, cellulose and its esters and derivatives, polyamides, polyester-polyethers, styrene-isoprenes, styrenebutadienes, thermoplastic polyolefins, styrene-saturated olefins, polyester-polyester, ethylene-vinyl acetate ethylene-ethyl acrylate, ionomers, and thermoplastic polydienes, or mixtures or blends thereof.

Graftable polymers may form covalent bonds to polysilicone surfaces through reactions that include nucleophile/electrophile reactions. Examples of nucleophile/electrophile reactions for the covalent linkage of a graftable polymer to a polysilicone surface include but are not limited to: substitution at electrophilic carbonyl centers, nucleophilic addition to ketenes, nucleophilic addition to isocyanates, nucleophilic addition to isothiocyanates, nucleophilic addition at activated silicon centers, nucleophilic substitution at activated silicon centers, nucleophilic displacement of an alkyl halide, nucleophilic displacement at an alkyl pseudohalide, addition/elimination at an activated carbonyl, 1,4-conjugate addition of a nucleophile to an α,β-unsaturated carbonyl, nucleophilic ring opening of an epoxide, nucleophilic aromatic substitution of an electron deficient arene, nucleophilic addition at activated phosphorous centers, nucleophilic addition at activated phosphorous centers, nucleophilic substitution at activated phosphorous centers, nucleophilic addition at activated sulfur centers, and nucleophilic substitution at activated sulfur centers. For example, the grafting moiety may be an electrophile as exemplified by compounds (1)-(4) that include activated silicon centers.

The polysilicone surfaces may further include tie coats such as acetoxysilane additives. Preferred acetoxysilane additives for the treatment of polysilicone surfaces include tert-butyloxy triacetoxysilane, ethyl triacetoxysilane (ETAS), and methyl triacetoxysilane (MTAS).

Graftable polymers can form covalent bonds to the surfaces of base polymers such as polyurethanes through reactions that include nucleophile/electrophile reactions. Examples of suitable nucleophile/electrophile reactions include but are not limited to: insertion by an electrophile into a C—H bond, insertion by an electrophile into an N—H bond, substitution at electrophilic carbonyl centers, nucleophilic addition to isocyanates, or addition/elimination at an activated carbonyl. UV labile grafting moieties such as compounds (5) and (6) can be used to form covalent bonds between the graftable polymer and the polyurethane surface.

Alternatively, graftable polymers may form covalent bonds to polyvinylchloride surfaces through reactions that include nucleophile/electrophile reactions. Examples of suitable nucleophile/electrophile reactions include but are not limited to: insertion by an electrophile into a C—H bond, insertion by an electrophile into an N—H bond, substitution at electrophilic carbonyl centers, nucleophilic addition to isocyanates, or addition/elimination at an activated carbonyl. Again, UV labile grafting moieties such as compounds (5) and (6) can be used to form covalent bonds between the graftable polymer and the polyvinylchloride surface.

Graftable polymers may form covalent bonds to latex surfaces through reactions that include but are not limited to coupling reactions. Examples of coupling reactions that can be useful for grafting to a latex surface are: hydrosilylation, Stille coupling, Suzuki coupling, Sonogashira coupling, Hiyama coupling, and the Heck reaction. Grafting moieties that include hydridosilanes (e.g. compound (7)) can be used to form covalent bonds between a graftable polymer and a latex surface.

The latex surfaces may further include alkoxysilane additives. Non-limiting examples of alkoxysilane additives include: $(OR)_3SiH$ wherein R can be methyl, ethyl, or acetyl; $(OR)_2(CH_3)SiH$ wherein R can be methyl, ethyl, or acetyl; or $(OR)(CH_3)_2SiH$ wherein R is methyl, ethyl, or acetyl.

The grafting of a graftable, pharmaceutically active polymer to a base polymer can benefit from the use of promoters and catalysts. Methods that may be used in grafting can be selected from: chemical treatment of the surface, photolytic activation, thermolytic activation, use of a catalyst, by other means known in the art, or by any combination of the methods listed. Catalysts may be employed for the grafting of a pharmaceutically active polymer to a base polymer. For pharmaceutically active polymers that include activated polysiloxanes as the grafting moiety, the use of catalysts such as dibutyltin dilaurate and dibutyltin octanoate may be employed. For pharmaceutically active polymers that include hydridosilanes as the grafting moiety, the use of Pt(0), Pt(II), or Pt(IV) catalysts may be employed. In the chemical treatment of a base polymer, the polymer may be treated with a tie coat (e.g., reactive silane reagents such as alkoxysilanes, acetoxysilanes, or trimethylsilylchloride), mineral acids such as HCl, $H_2SO_4$, or $HNO_3$ or the polymer may be treated with bases such as NaOH or KOH.

Ceramics

The graftable, pharmaceutically active polymers of the invention may be grafted to a ceramic surface. Examples of ceramics that may be used in the invention are $Ca_5(PO_4)_3(OH)$ (hydroxyapatite), $TiO_2$, $Al_2O_3$, $ZrO_2$ (zirconia), $SiO_2$, or ZnO, or any composite thereof.

In one example, graftable polymers may form covalent bonds to ceramic surfaces through reactions that include nucleophile/electrophile reactions. Such reactions can include, but are not limited to: substitution at electrophilic carbonyl centers, addition to ketenes, nucleophilic addition to isocyanates, nucleophilic addition to isothiocyanates, nucleophilic substitution at activated silicon centers, nucleophilic displacement of an alkyl halide, nucleophilic displacement at an alkyl pseudohalide, addition/elimination at an activated carbonyl, 1,4-conjugate addition of a nucleophile to an α,β- unsaturated carbonyl, nucleophilic ring opening of an epoxide, nucleophilic aromatic substitution of an electron deficient arene, nucleophilic substitution at activated phosphorous centers, and nucleophilic substitution at activated sulfur centers. In preferred embodiments, the grafting moiety of the polymer can be an electrophilic, activated silicon center (e.g. compounds (1)-(4)).

The grafting of a graftable, pharmaceutically active polymer to a ceramic surface may benefit from the chemical treatment of the ceramic. In the chemical treatment of the ceramic, the ceramic may be treated with: a tie coat (e.g., reactive silane reagents such as alkoxysilanes, acetoxysilanes, or trimethylsilylchloride); mineral acids such as HCl, $H_2SO_4$, or $HNO_3$; or with bases such as NaOH or KOH. For example, mineral acids or alkoxide bases can be used in the grafting to ceramic surfaces.

Metals

The graftable, pharmaceutically active polymers of the invention may be grafted to the surface of a metal or an alloy thereof. Exemplary metals useful in the invention are: aluminum, cadmium, chromium, cobalt, copper, gold, iridium, iron, magnesium, molybdenum, nickel, palladium, platinum, silver, titanium, and zinc. Exemplary alloys are: cobalt/chromium alloys; silver alloys; stainless steel, such as stainless steel 316; and titanium alloys, such as nickel/titanium alloys (e.g. Nitinol). Other exemplary metallics include pyrolytic carbon. In some embodiments, graftable polymers may form covalent bonds to metal surfaces through reactions that include nucleophile/electrophile reactions. In one example, UV labile grafting moieties such as compounds (5) and (6) can be used to form covalent bonds between the graftable polymer and the metal surface.

Tie Coats

Exemplary chemical additives useful in the invention include tie coats. Tie coats can be small molecules, polymers, or any mixture thereof, and are additives that are used to improve adhesion of a graftable polymer, mixture of graftable polymers, or any composition thereof, to a surface. Tie coats may be applied to a surface prior to coating with a graftable polymer or may be applied to a surface as part of an mixture that includes a graftable polymer. For example, tie coats can be applied to a surface (e.g., the surface of a medical device) as a thin layer (e.g., a layer ranging between 5-80 μM or 5-20 μM in thickness) prior to application of the graftable polymer. Alternatively, the tie coat, or mixture thereof, can be combined with the graftable polymer, and the resulting mixture can then be applied to a surface (e.g., the surface of a medical device). Preferably, the tie coat is applied to a surface as a mixture with the graftable polymer.

The ratio of a tie-coat to the graftable polymer can also be varied (e.g., the weight:weight ("w/w") ratio of the graftable polymer:tie coat reagent can range from, for example, 1:5 to 50:1). For example, the range of the polymer:tie coat reagent (w/w) can be 2:1, 1:1, or 1:2. Tie coats used in the invention can be applied as a solution in a solvent (e.g., THF). These solutions may also include a graftable polymer, or mixtures thereof.

Without being bound by theory, the larger the ratio of drug polymer to tie coat on the surface, the greater the concentration of drug is available to be released on the surface. Accordingly, the ratio of graftable polymer:tie coat can be adjusted in order to produce the desired drug elution rate (e.g., a 2:1 ratio of polymer:tie coat can lead to faster elution of the drug compared to a 1:2 ratio; see, for example, FIG. 10). The rate of release of a drug can also be affected by the method of application of the tie coat (i.e., as a separate layer or as part of an admixture that includes the graftable polymer).

The process of coating an article by applying a tie coat and graftable polymer can be repeated as described herein in order to achieve the desired coating thickness. The tie coat and graftable polymer applied in each coating cycle can be the same or different tie coat and graftable polymer that were previously applied. Similarly, the ratios of the tie coat and graftable polymer (e.g., the w/w ratio of a mixture of tie-coat and graftable polymer) can be the same or different in each coating cycle.

Exemplary, non-limiting tie coats include Dow Corning® Q7-2360 and MDX4-42 tie coats, alkoxysilanes, acetoxysilanes such as $(AcO)_3Si(O^tBu)$ ("TEAS"), $(AcO)_3Si(OEt)$ ("ETAS"), $(AcO)_3Si(OMe)$ ("MTAS"), and functionalized small molecule and polymeric silicon reagents such as those shown in Scheme 1.

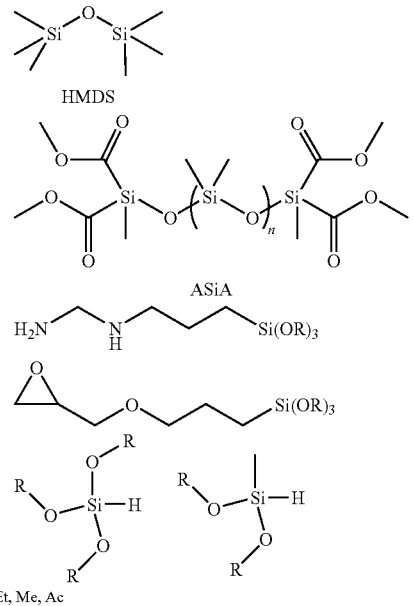

Scheme 1

In addition to the combinations of tie coats and surfaces described herein, Table 1 provides representative surfaces and exemplary, non-limiting tie-coats that can be used in combination with the surface and a graftable polymer as described herein.

TABLE 1

| Surface | Exemplary Tie Coats |
|---|---|
| Stainless steel | Mixture of epoxy resin and vinylpyrrolidone-vinyl acetate copolymers; styrene acrylic aqueous dispersion; Mixture of ethylene acrylic acid copolymer and melamine resin; Mixture of ethylene acrylic acid copolymer, melamine resin, hydroxyl functionalized acrylic polymer, and isocyanate polymer; Mixture of carboxyl functionalized acrylic polymer and epoxy resin; acrylic dispersion polymer; Mixture of polysilicone, alkoxysilane, and acetoxysilanes. |
| Polyethylene | Mixture of ethylene acrylic acid copolymers, melamine resin, hydroxyl functionalized acrylic polymers, and isocyanate polymers; Mixture of polysilicone, alkoxysilane, and acetoxysilanes. |
| Silicone | Mixture of ethylene acrylic acid copolymers, melamine resin, hydroxyl functionalized acrylic polymers, and isocyanate polymers; |

TABLE 1-continued

| Surface | Exemplary Tie Coats |
|---|---|
| Natural rubber | Mixture of polysilicone, alkoxysilane, and acetoxysilanes. Mixture of ethylene acrylic acid copolymers, melamine resin, hydroxyl functionalized acrylic polymers, and isocyanate polymers; |
| Poly-urethane | Mixture of polysilicone, alkoxysilane, and acetoxysilanes. Mixture of ethylene acrylic acid copolymers, melamine resin, hydroxyl functionalized acrylic polymers, and isocyanate polymers; |
| Polyester | Mixture of polysilicone, alkoxysilane, and acetoxysilanes. Mixture of ethylene acrylic acid copolymers, melamine resin, hydroxyl functionalized acrylic polymers, and isocyanate polymers; Mixture of polysilicone, alkoxysilane, and acetoxysilanes. |

Hydrolysable Coupling Segments and Polymamide Linkers

Polyamide linkers incorporated in the graftable, pharmaceutically active polymers of the invention (e.g., C2 in Formulas (III), (IV), (VII), and (VIII)) include natural amino acids coupled through amide linkages in linear or branched sequences. The polyamide linkers are designed to be susceptible to hydrolysis by particular endopeptidase enzymes, such as *Staphylococcus aureus* serine glutamyl endopeptidase, V8 protease, metalloproteinases including aureolysin and MMP-9, and exopeptidases such as carboxypeptidase A, carboxypeptidase B, aminopeptidase N/CD, and aminopeptidase P, that are upregulated during a physiological response or pathological process.

Hydrolysis of the polyamide linker occurs at specific protease cleavage recognition sites. In particular, MMP-9 is known to recognize and cleave several consensus sequences; including Pro-X-X-Hy-(Ser/Thr), Gly-Leu-(Lys/Arg), Arg-Arg-X-(Ile/Lys), and Arg-X-(Ile/Lys), where X is any residue and Hy is a hydrophobic residue. MMP-9 has a unique preference for Arg at both $P_2$ and $P_1$ and a preference for Ser/Thr at $P_2$. V8 protease favors glutamic acid and Pro or Leu at the $P_1$ and $P_2$ position, respectively, while the S3 subsite of V8 protease prefers leucine. Aureolysin has a low substrate specificity and cleaves bonds on the N-terminal side of bulky, aliphatic, or hydrophobic residues. Furthermore, human exopeptidases, carboxypeptidase B and aminopeptidases N/CD, target basic residues (Arg/Lys) and Ala, respectively.

To prepare a polymer susceptible to degradation by Cathepsin K, the polyamide linker can include one of the following peptide sequences specifically recognized by this enzyme: KLRFSKQEDD; KXPGSKQEDD; and KPXGSKQEDD (see, for example, Alves et al., *Biochem. J.* 373:981 (2003)).

To prepare a polymer susceptible to degradation in the presence of *Candida albicans*, the polyamide linker can include a peptide sequence recognized by a peptidase enzyme expressed by this organism (e.g., aspartyl proteinases expressed by *C. albicans* recognize the peptide sequence SLASPPTSLVF)(see, for example, Putnam et al., *J. Biol. Chem.* 254:2865 (1979)).

Polyamide linkers may incorporate non-natural or D-amino acids and remain susceptible to hydrolysis by secreted prokaryotic proteases. The V8 protease has a large hydrophobic pocket at its P1' position and can digest a p-nitroanilide substrate. Secreted Prokaryotic proteases may also recognize D-amino acids and preferentially hydrolyze the polyamide linker in the presence of Eukaryotic proteases Polyamide linkers remain stable to exopeptidase activity until hydrolysis by endopeptidases creates polyamide fragments with free carboxy- or amino-termini. The need for aminopeptidases may be minimized by locating endopeptidase cleavage sites at the C-terminus of polyamide linkers attached to the biologically active agent.

Because protease recognition sequences are generally only a few amino acids in length, a relatively short polyamide linker can contain several cleavage recognition sites. Polyamide linkers used in the invention can range from 2 to 60 amino acids in length.

Additional examples of hydrolysable coupling segments and polymamide linkers are disclosed in WO2005110485 and U.S. Patent Publications 20050255079 and 20050255082, all of which are hereby incorporated by reference.

Biologically Active Agents

Biologically active agents that can be incorporated into the graftable pharmaceutically active polymers of the invention include therapeutic, diagnostic, and prophylactic agents. They can be naturally occurring compounds, synthetic organic compounds, or inorganic compounds. Agents that can be incorporated into the pharmaceutically active polymers of the invention include, but are not limited to carbohydrates, anti-microbials, antiproliferative agents, rapamycin macrolides, analgesics, anesthetics, antiangiogenic agents, vasoactive agents, anticoagulants, immunomodulators, cytotoxic agents, antiviral agents, antithrombotic drugs, such as terbrogel and ramatroban, antibodies, neurotransmitters, psychoactive drugs, oligonucleotides, proteins, lipids, and combinations thereof. A pharmaceutically active polymer can also include more than one biologically active agent. For example, a pharmaceutically active polymer may include two biologically active agents. The grafting of mixtures and blends of different pharmaceutically active polymers is also useful in the articles of the invention.

In certain embodiments, the biological agent includes two functional groups selected from hydroxyl, amine, carboxylic acid or sulfonic acid so that it can be tethered to one or more oligomeric segments. For example, Ciprofloxacin, which contains a free secondary amine and carboxyl groups, can be covalently tethered between two oligomeric segments and incorporated into a polymer that includes one or more graftable moieties.

Exemplary therapeutic agents which can be incorporated into the graftable pharmaceutically active polymers of the invention include, without limitation, growth hormone, for example human growth hormone, calcitonin, granulocyte macrophage colony stimulating factor (GMCSF), ciliary neurotrophic factor, and parathyroid hormone. Other specific therapeutic agents include parathyroid hormone-related peptide, somatostatin, testosterone, progesterone, estradiol, nicotine, fentanyl, norethisterone, clonidine, scopolomine, salicylate, salmeterol, formeterol, albeterol, valium, heparin, dermatan, ferrochrome A, erythropoetins, diethylstilbestrol, lupron, estrogen estradiol, androgen halotestin, 6-thioguanine, 6-mercaptopurine, zolodex, taxol, lisinopril/zestril, streptokinase, aminobutylric acid, hemostatic aminocaproic acid, parlodel, tacrine, potaba, adipex, memboral, phenobarbital, insulin, gamma globulin, azathioprine, papein, acetaminophen, ibuprofen, acetylsalicylic acid, epinephrine, flucloronide, oxycodone percoset, dalgan, phreniline butabital, procaine, novocain, morphine, oxycodone, aloxiprin, brofenac, ketoprofen, ketorolac, hemin, vitamin B-12, folic acid, magnesium salts, vitamine D, vitamin C, vitamin E, vitamin A, Vitamin U, vitamin L, vitamin K, pantothenic acid, aminophenylbutyric acid, penicillin, acyclovir, oflaxacin, amoxicillin, tobramycin, retrovior, epivir, nevirapine, gentamycin, duracef, ablecet, butoxycaine, benoxinate, tropenzile, diponium salts, butaverine, apoatropine, feclemine, leiopyrrole, octamylamine, oxybutynin, albuterol, metaproterenol, beclomethasone dipropionate, triamcinolone acetamide, budesonide acetonide, ipratropium bromide, flunisolide, cromolyn sodium, ergotamine tartrate, and protein or peptide drugs such as TNF antagonists or interleukin antagonists. For example, the biologically active agent can be an anti-inflammatory agent, such as an NSAID, corticosteriod, or COX-2 inhibitor, e.g., rofecoxib, celecoxib, valdecoxib, or lumiracoxib. The therapeutic agent may also include antibiotics.

Exemplary diagnostic agents which can be incorporated into the graftable pharmaceutically active polymers of the invention include, without limitation, imaging agents, such as those that are used in positron emission tomography (PET), computer assisted tomography (CAT), single photon emission computerized tomography, X-ray, fluoroscopy, and magnetic resonance imaging (MRI). Suitable materials for use as contrast agents in MRI include gadolinium chelates, as well as iron, magnesium, manganese, copper, and chromium chelates. Examples of materials useful for CAT and X-rays include iodine based materials.

Rapamycin Macrolides

Rapamycin macrolides can be incorporated into the graftable pharmaceutically active polymers of the invention. Rapamycin (Sirolimus) is an immunosuppressive lactam macrolide that is produced by *Streptomyces hygroscopicus*. See, for example, McAlpine, J. B., et al., J. Antibiotics 44: 688 (1991); Schreiber, S. L., et al., J. Am. Chem. Soc. 113: 7433 (1991); and U.S. Pat. No. 3,929,992, incorporated herein by reference. Exemplary rapamycin macrolides that can be used in the methods and compositions of the invention include, without limitation, rapamycin, CCI-779, Everolimus (also known as RAD001), and ABT-578 (40-epi-(N1-tetrazolyl)-rapamycin, see, for example, Pagano T. G., *Magn. Reson. Chem.* 43:174 (2005)). CCI-779 is an ester of rapamycin (42-ester with 3-hydroxy-2-hydroxymethyl-2-methylpropionic acid), disclosed in U.S. Pat. No. 5,362,718. Everolimus is an alkylated rapamycin (40-O-(2-hydroxyethyl)-rapamycin, disclosed in U.S. Pat. No. 5,665,772.

Antiproliferative Agents

Antiproliferative agents can be incorporated into the graftable pharmaceutically active polymers of the invention. Exemplary antiproliferative agents which can be used in the methods and compositions of the invention include, without limitation, mechlorethamine, cyclophosphamide, iosfamide, melphalan, chlorambucil, uracil mustard, estramustine, mitomycin C, AZQ, thiotepa, busulfan, hepsulfam, carmustine, lomustine, semustine, streptozocin, dacarbazine, cisplatin, carboplatin, procarbazine, methotrexate, trimetrexate, fluouracil, floxuridine, cytarabine, fludarabine, capecitabine, azacitidine, thioguanine, mercaptopurine, allopurine, cladribine, gemcitabine, pentostatin, vinblastine, vincristine, etoposide, teniposide, topotecan, irinotecan, camptothecin, 9-aminocamptothecin, paclitaxel, docetaxel, daunorubicin, doxorubicin, dactinomycin, idarubincin, plicamycin, mitomycin, amsacrine, bleomycin, aminoglutethimide, anastrozole, finasteride, ketoconazole, tamoxifen, flutamide, leuprolide, goserelin, Gleevec™ (Novartis), leflunomide (Pharmacia), SU5416 (Pharmacia), SU6668 (Pharmacia), PTK787 (Novartis), Iressa™ (AstraZeneca), Tarceva™, (Oncogene Science), trastuzumab (Genentech), Erbitux™ (ImClone), PKI166 (Novartis), GW2016 (GlaxoSmithKline), EKB-509 (Wyeth), EKB-569 (Wyeth), MDX-H210 (Medarex),2C4 (Genentech), MDX-447 (Medarex), ABX-EGF (Abgenix), CI-1033 (Pfizer), Avastin™ (Genentech), IMC-1C11 (ImClone), ZD4190 (AstraZeneca), ZD6474 (AstraZeneca), CEP-701 (Cephalon), CEP-751 (Cephalon), MLN518 (Millenium), PKC412 (Novartis), 13-cis-retinoic acid, isotretinoin, retinyl palmitate, 4-(hydroxycarbophenyl) retinamide, misonidazole, nitracrine, mitoxantrone, hydroxyurea, L-asparaginase, interferon alfa, AP23573, Cerivastatin, Troglitazone, CRx-026DHA-paclitaxel, Taxoprexin, TPI-287, Sphingosine-based lipids, and mitotane.

Corticosteroids

Corticosteroids can be incorporated into the graftable pharmaceutically active polymers of the invention. Exemplary corticosteroids which can be used in the methods and compositions of the invention include, without limitation, 21-acetoxypregnenolone, alclomerasone, algestone, amcinonide, beclomethasone, betamethasone, betamethasone valerate, budesonide, chloroprednisone, clobetasol, clobetasol propionate, clobetasone, clobetasone butyrate, clocortolone, cloprednol, corticosterone, cortisone, cortivazol, deflazacon, desonide, desoximerasone, dexamethasone, diflorasone, diflucortolone, difluprednate, enoxolone, fluazacort, flucloronide, flumethasone, flumethasone pivalate, flunisolide, flucinolone acetonide, fluocinonide, fluorocinolone acetonide, fluocortin butyl, fluocortolone, fluorocortolone hexanoate, diflucortolone valerate, fluorometholone, fluperolone acetate, fluprednidene acetate, fluprednisolone, flurandenolide, formocortal, halcinonide, halometasone, halopredone acetate, hydrocortamate, hydrocortisone, hydrocortisone acetate, hydrocortisone butyrate, hydrocortisone phosphate, hydrocortisone 21-sodium succinate, hydrocortisone tebutate, mazipredone, medrysone, meprednisone, methylprednicolone, mometasone furoate, paramethasone, prednicarbate, prednisolone, prednisolone 21-diedryaminoacetate, prednisolone sodium phosphate, prednisolone sodium succinate, prednisolone sodium 21-m-sulfobenzoate, prednisolone sodium 21-stearoglycolate, prednisolone tebutate, prednisolone 21-trimethylacetate, prednisone, prednival, prednylidene, prednylidene 21-diethylaminoacetate, tixocortol, triamcinolone, triamcinolone acetonide, triamcinolone benetonide and triamcinolone hexacetonide. Structurally related corticosteroids having similar anti-inflammatory properties are also intended to be encompassed by this group.

NSAIDs

Non-steroidal anti-inflammatory drugs (NSAIDs) can be incorporated into the graftable pharmaceutically active polymers of the invention. Exemplary NSAIDs which can be used in the methods and compositions of the invention include, without limitation, naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid (salsalate), fenoprofen, flurbiprofen, ketoprofen, meclofenamate sodium, meloxicam, oxaprozin, sulindac, and tolmetin.

Analgesics

Analgesics can be incorporated into the graftable pharmaceutically active polymers of the invention. Exemplary analgesics that can be used in the methods and compositions of the invention include, without limitation, fentanyl, morphine, codeine, heroin, ethylmorphine, O-carboxymethylmorphine, O-acetylmorphine, hydrocodone, hydromorphone, oxymorphone, oxycodone, dihydrocodeine, thebaine, metopon, ethorphine, acetorphine, diprenorphine, buprenorphine, phenomorphan, levorphanol, ethoheptazine, ketobemidone, dihydroetorphine and dihydroacetorphine.

Antimicrobials

Antimicrobials can be incorporated into the graftable pharmaceutically active polymers of the invention. Exemplary antimicrobials which can be used in the methods and compositions of the invention include, without limitation, penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmatozole, cefotaxime, ceftizoxime, ceftriaxone, cefoperazone, ceftazidime, cefixime, cefpodoxime, ceftibuten, cefdinir, cefpirome, cefepime, chlorhexidine, BAL5788, BAL9141, imipenem, ertapenem, meropenem, astreonam, clavulanate, sulbactam, tazobactam, streptomycin, neomycin, kanamycin, paromycin, gentamicin, tobramycin, amikacin, netilmicin, spectinomycin, sisomicin, dibekalin, isepamicin, tetracycline, chlortetracycline, demeclocycline, minocycline, oxytetracycline, methacycline, doxycycline, erythromycin, azithromycin, clarithromycin, telithromycin, ABT-773, lincomycin, clindamycin, vancomycin, oritavancin, dalbavancin, teicoplanin, quinupristin and dalfopristin, sulphanilamide, para-aminobenzoic acid, sulfadiazine, sulfisoxazole, sulfamethoxazole, sulfathalidine, linezolid, nalidixic acid, oxolinic acid, norfloxacin, perfloxacin, enoxacin, ofloxacin, ciprofloxacin, temafloxacin, lomefloxacin, fleroxacin, grepafloxacin, sparfloxacin, trovafloxacin, clinafloxacin, gatifloxacin, moxifloxacin, gemifloxacin, sitafloxacin, metronidazole, daptomycin, garenoxacin, ramoplanin, faropenem, polymyxin, tigecycline, AZD2563, and trimethoprim.

Membrane Active Biocides

One exemplary, non-limiting class of anti-microbials useful in the polymers and articles of the invention are membrane active biocides. Membrane active biocides which can be used in the polymers and articles of the invention include, without limitation, chlorhexidine, polymyxin B-nonapeptide, bacitracin, monobactams (e.g., aztreonam, carumonam, or tigemonan), benzalkonium salts, and metal chelators, such as ethylenediaminetetraacetate (EDTA).

Fluoroquinolones

A second exemplary, non-limiting class of anti-microbials are fluoroquinolones. Examples of fluoroquinolones useful in the polymers and articles of the invention include, but are not limited to, those described in patent publications BE870576; DE3142854; EP047005; EP206283; BE887574; EP221463; EP140116; EP131839; EP154780; EP078362; EP310849; EP520240; and U.S. Pat. Nos. 4,448,962; 4,499,091; 4,704,459; 4,795,751; 4,668,784; and 5,532,239, each of which is incorporated herein by reference.

Additional exemplary fluoroquinolones which can be used in the polymers and articles of the invention include, without limitation, ciprofloxacin (commercially available as Cipro®), enrofloxacin (commercially available as Baytril®), enoxacin (commercially available as Penetrex®), gatifloxacin (commercially available as Tequin®), gemifloxacin (commercially available as Factive®), levofloxacin (commercially available as Levaquin®), lomefloxacin (commercially available as Maxaquin®), moxifloxacin (commercially available as Avelox®), norfloxacin (commercially available as Noroxin®), ofloxacin (commercially available as Floxin®), sparfloxacin (commercially available as Zagam®), trovafloxacin (commercially available as Trovan®), difloxacin, cinofloxacin, pefloxacin, tosufloxacin, temafloxacin, fleroxacin, amifloxacin, binfloxacin, danofloxacin, marbofloxacin, ruflocaxin, and sarafloxacin.

Local Anesthetics

Local anesthetics can be incorporated into the graftable pharmaceutically active polymers of the invention. Exemplary local anesthetics that can be used in the methods and compositions of the invention include, without limitation, cocaine, procaine, lidocaine, prilocalne, mepivicaine, bupivicaine, articaine, tetracaine, chloroprocaine, etidocaine, and ropavacaine.

Antispasmodics

Antispasmodics can be incorporated into the graftable pharmaceutically active polymers of the invention. Exemplary antispasmodics that can be used in the methods and compositions of the invention include, without limitation, anticholinergics and other therapeutics including: atropine, belladonna, Bentyl® (dicyclomine), Cystospaz® (hyoscyamine), darifenacin, Detrol® (tolterodine), Ditropan® (oxybutynin), Donnatal®, Donnazyme®, fasudil, Flexeril® (clobenzaprine), glycopyrrolate, Levsin®, Levsinex®, Librax®, Malcotran® or Novatrine® (homatropine methylbromide), Novartin® (hydergine), oxyphencyclimine, Pamine®) (methscopolamine), prozapine, pinaverium, solifenacin succinate, tiquizium, and trospium.

Coated Articles

A wide variety of articles can be coated with the graftable pharmaceutically active polymers of the invention. For example, articles which contact bodily fluids, such as medical devices can be coated to improve their biocompatibility. The medical devices include, without limitation, catheters, guide wires, vascular stents, micro-particles, electronic leads, probes, sensors, drug depots, transdermal patches, vascular patches, blood bags, and tubing. The medical device can be an implanted device, percutaneous device, or cutaneous device. Implanted devices include articles that are fully implanted in a patient, i.e., are completely internal. Percutaneous devices include items that penetrate the skin, thereby extending from outside the body into the body. Cutaneous devices are used superficially. Implanted devices include, without limitation, prostheses such as pacemakers, electrical leads such as pacing leads, defibrillarors, artificial hearts, ventricular assist devices, anatomical reconstruction prostheses such as breast implants, artificial heart valves, heart valve stents, pericardial patches, surgical patches, coronary stents, vascular grafts, vascular and structural stents, vascular or cardiovascular shunts, biological conduits, pledges, sutures, annuloplasty rings, stents, staples, valved grafts, dermal grafts for wound healing, orthopedic spinal implants, orthopedic pins, intrauterine devices, urinary stents, maxial facial reconstruction plating, dental implants, intraocular lenses, clips, sternal wires, bone, skin, ligaments, tendons, and combination thereof. Percutaneous devices include, without limitation, catheters or various types, cannulas, drainage tubes such as chest tubes, surgical instruments such as forceps, retractors, needles, and gloves, and catheter cuffs. Cutaneous devices include, without limitation, burn dressings, wound dressings and dental hardware, such as bridge supports and bracing components.

Combination Therapies

Any of the polymers and articles of the invention may include two or more biologically active agents. For example, a graftable, pharmaceutically active polymer of the invention may include two or more biologically active agents. In another example, two or more pharmaceutically active polymers that each include a different biologically active agent can be used in the grafted articles of the invention.

In a non-limiting example, the polymers and articles of the invention can include two or more anti-microbials. The grafted articles of the invention can also include two different pharmaceutically active polymers that each include a different anti-microbial. One exemplary, non-limiting combination useful in the polymers and articles of the invention is that of a membrane active biocide and a fluoroquinolone. For example, the polymers and articles of the invention can include both a membrane active biocide and a fluoroquinolone. In some embodiments, an article of the invention may have grafted to its surface pharmaceutically active polymers that include a membrane active biocide and other pharmaceutically active polymers that include a fluoroquinolone. In certain embodiments, the two or more pharmaceutically active polymers may be blended or combined. The mixture or combination of graftable polymers can be grafted to the surface of an article. In yet another embodiment of the invention, the graftable pharmaceutically active polymers that include different biologically active agents are grafted separately onto the surface. In certain polymers and articles of the invention, the membrane active biocide is chlorhexidine and the fluoroquinolone is ciprofloxacin.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

Example 1

Synthesis of Polysilicones Including an Activated Silicon Grafting Moiety with Amine End Groups Polysilicones including activated silicon centers and amine end groups were used in the synthesis of graftable, pharmaceutically active polymers. A polysilicone including an activated silicon center as a grafting moiety was prepared according to Scheme 2. A polysilicone (Compound (8)) was treated with an amine-containing silicon reagent such as compound (9) to yield a polysilicone that has amine end groups (compound (2)). In this procedure, compound (8) was stripped of water by heating to 100° C. under vacuum (2-5 mm Hg) for 1 hour. The temperature was then reduced to 75° C. and aminopropyltrialkoxysilane (compound 9) was then added. The system remained under vacuum for 4 hours to remove the ethanol formed from the condensation process. A clear colorless fluid was then obtained. $^1$H NMR (400 MHz, CDCl$_3$). δ: 3.75 (q, OCH$_2$CH$_3$), 2.64 (t, CH$_2$CH$_2$CH$_2$), 1.19 (t, OCH$_2$CH$_3$, 0.00 (s, Si(CH$_3$).

Example 2

Synthesis of Polysilicones Including an Activated Silicon Grafting Moiety with Hydroxy End Groups Polysilicones including activated silicon centers and hydroxy end groups may be used in the synthesis of graftable, pharmaceutically active polymers. A polysilicone including an activated silicon center as a grafting moiety may be prepared according to Scheme 3. A polysilicone (Compound (8)) may be treated with a hydroxy-containing silicon reagent such as compound (10) to yield an activated polysilicone that has hydroxy end groups (compound (4)).

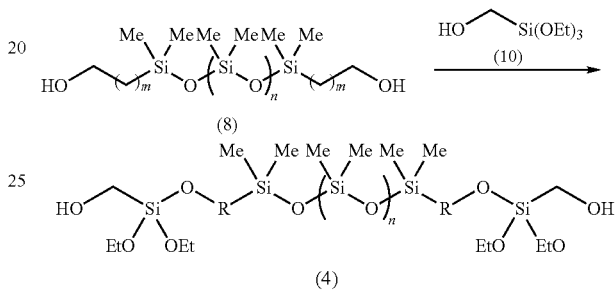

Example 3

Synthesis of Polysilicones Including a Hydridosilane Grafting Moiety with Amine End Groups Monomers including hydridosilanes are suitable for the synthesis of graftable, pharmaceutically active polymers and can be prepared according to Scheme 4. A silane reagent such as compound (11) can be used in a Pt-catalyzed hydrosilylation of an olefinic substrate such as an N-protected allylamine (compound (12)). The resulting product (compound (13)) may then be treated with a reducing agent such as LiAlH$_4$ followed by N-deprotection to afford the desired hydridosilane product (compound (5)).

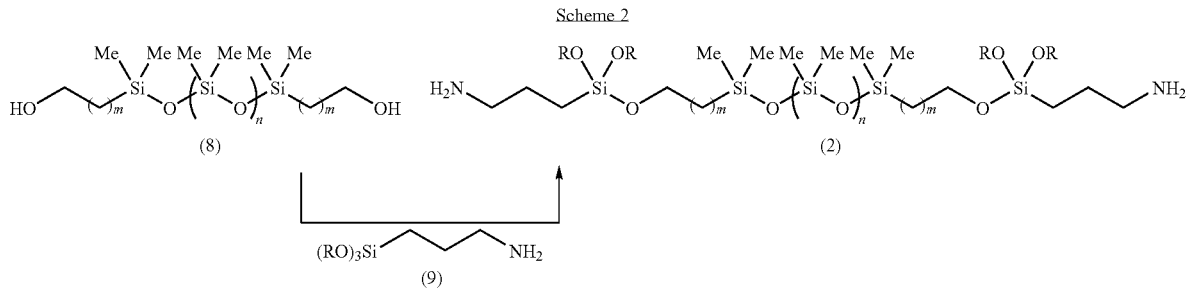

Scheme 4

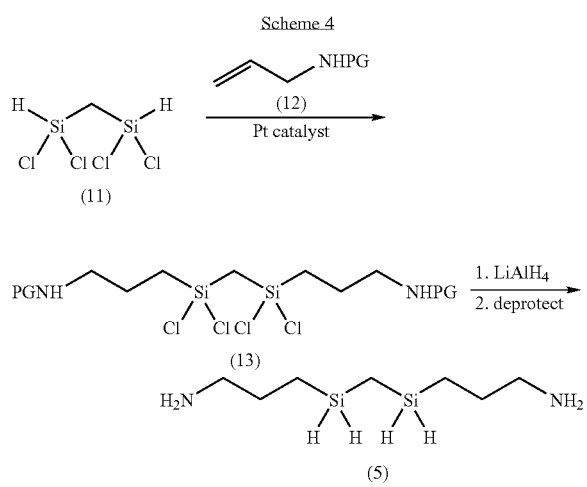

Example 4

Synthesis of a Diamine or a Diol Including an Azide Grafting Moiety

Diamines and diols including a grafting moiety including an azide were prepared according to Scheme 5. A precursor including an activated carboxylic acid group (compound (14)) was treated with reagents such as compounds (15) and (16). These latter reagents employed suitable protecting groups (PG) when required on the terminal amine and hydroxyl functional groups, respectively. Deprotection subsequently afforded the corresponding monomers (6) and (7). Monomer (6) is also referred to as "Reagent A" or "SANPAH" and is commercially available from Thermo Scientific.

Scheme 5

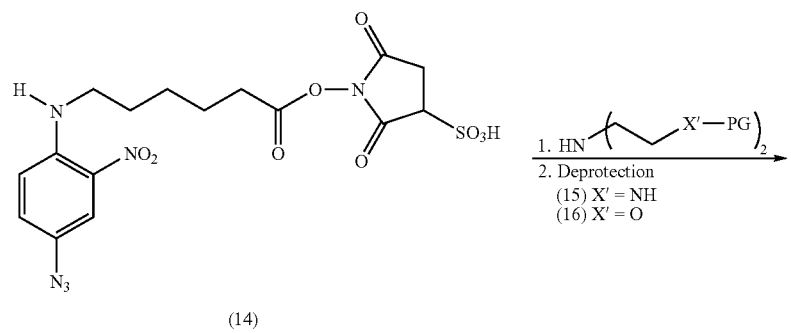

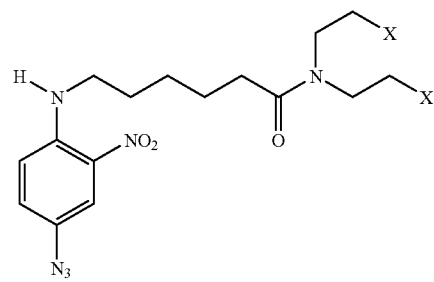

(6) X = NH$_2$
(7) X = OH

For example, diethanolamine (compound (16)) was added dropwise to a cooled (0° C.) solution of compound (14) in DMF. The orange solution was stirred overnight with warming. The solvent was removed under reduced pressure. The resulting solid residue was dissolved in ethyl acetate and transferred to a separatory funnel where the organic layer was washed with brine. The combined aqueous layers were back extracted with ethyl acetate. The organic layers were combined, dried with sodium sulfate and the solvent was removed under reduced pressure to yield compound (7) which was used without further purification. $^1$H NMR (400 MHz, CDCl$_3$). δ: 7.78 (s, 1H, Ph-H), 7.06 (dd, J=2.76 Hz, J=8.1 Hz, 1H, Ph-H), 6.8 (d, J=8.1 Hz, 1H, Ph-H), 3.76 (dt, J=5.0 Hz, J=30.8 Hz, 4H, NCH$_2$CH$_2$OH), 3.47 (dt, J=5.0 Hz, J=30.8 Hz, 4H, NCH$_2$CH$_2$OH), 3.25 (t, J=7.0 Hz, 2H, Ph-NHCH$_2$CH$_2$CH$_2$CH$_2$CH$_2$CO), 2.38 (t, J=7.32 Hz, 2H, Ph-NHCH$_2$CH$_2$CH$_2$CH$_2$CH$_2$CO), 1.67 (m, 4H, Ph-NHCH$_2$CH$_2$CH$_2$CH$_2$CH$_2$CO), 1.42 (m, 2H, Ph-NHCH$_2$CH$_2$CH$_2$CH$_2$CH$_2$CO), 1.18 (bs, 2H, OH); $^{13}$C NMR (400 MHz, CDCl$_3$) δ: 175.3, 143.6, 128.5, 128.0, 116.2, 115.8, 62.0, 61.0, 52.2, 50.6, 43.2, 29.0, 26.9, 24.9.

Example 5

Synthesis of Graftable, Pharmaceutically Active Polymers Including Activated Silicon Grafting Moieties Scheme 6
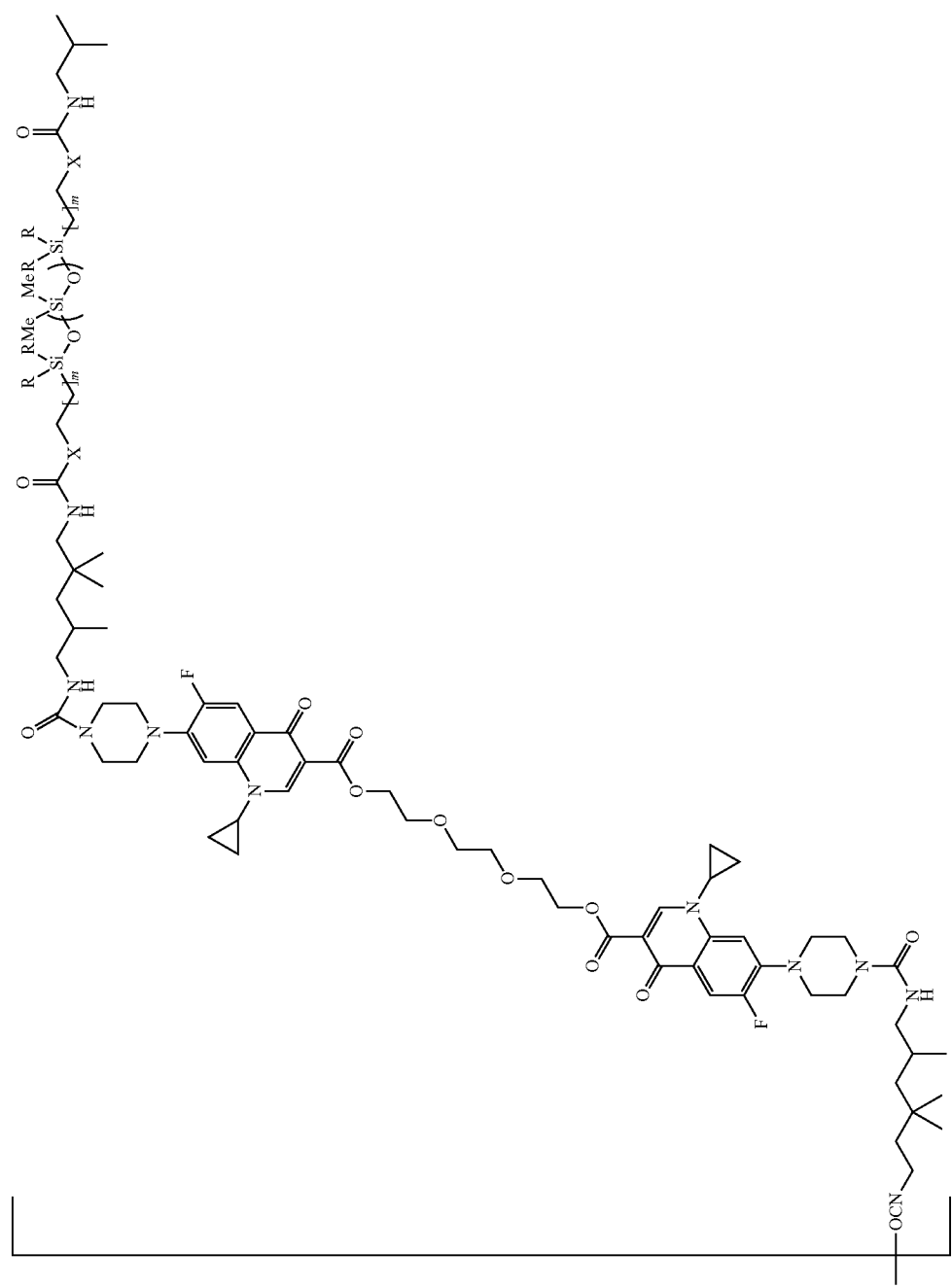

-continued
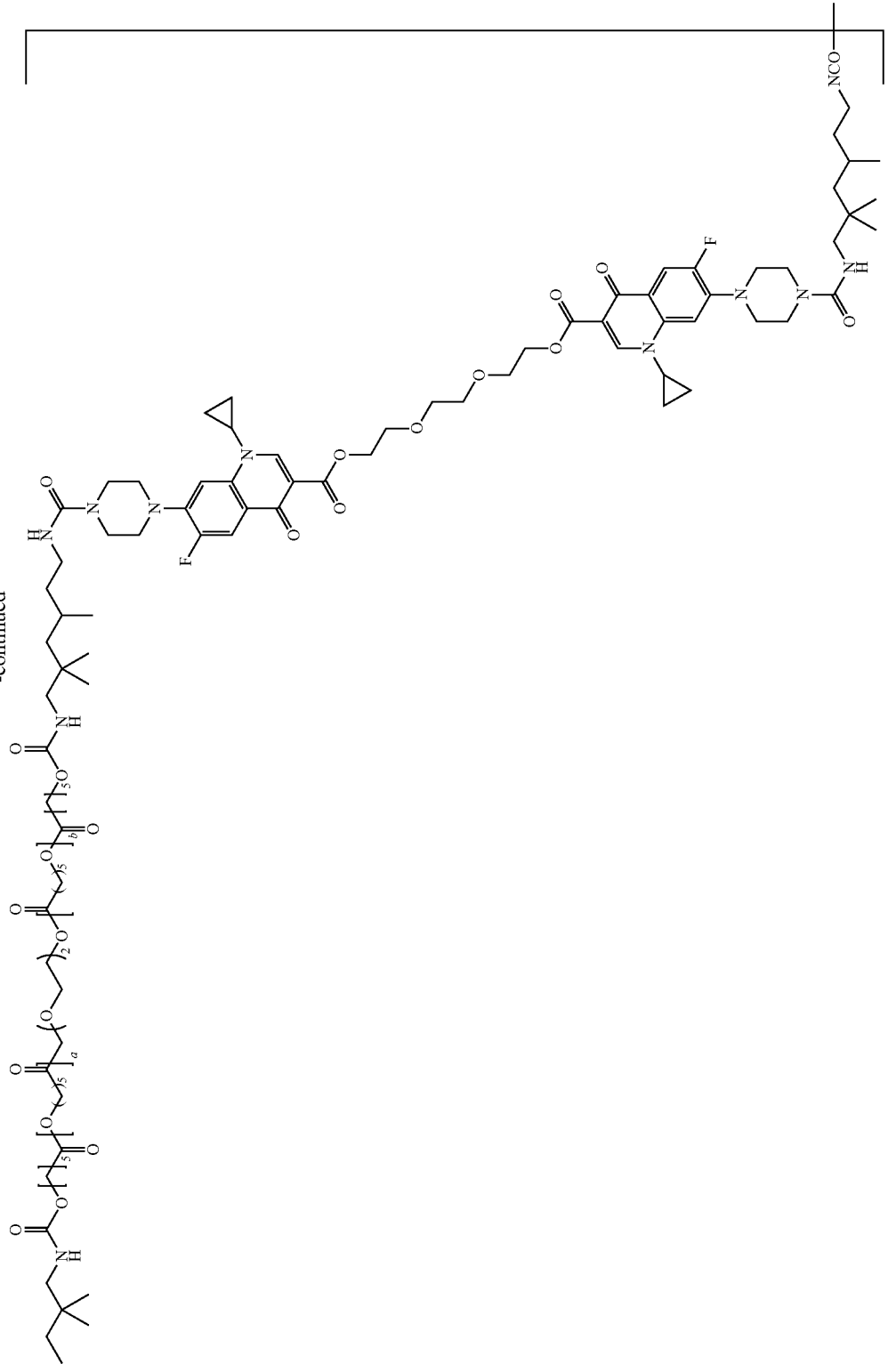
17 X = NH, R = Me
18 X = NH, R = OEt
19 X = O, R = Me
20 X = O, R = OEt Graftable pharmaceutically active polymers including activated silicon grafting moieties are synthesized by prepolymerizing a mixture of the selected polysilicone (e.g. compounds (2) or (4)) in polycaprolactone diol (PCL) with a diisocyanate in the presence of a catalyst. In the second stage of polymerization, the pharmaceutically-active component and any additional catalyst are added to afford the desired graftable, pharmaceutically active polymers.

The synthesis of a polymer from reagents that include compound (2), PCL, and 2,2,4-trimethylhexamethylene diisocyanate (THDI) was accomplished according to the following procedure:

A mixture of 10% (w/w) compound (2) in PCL (2.0 equivalents relative to CP), THDI (3.1 equivalents), and dibutyltin dilaurate (DBTL; 0.2 equivalents) was heated in dimethylsulfoxide (DMSO) at 65° C. for 1.5 hours. At that time, a DMSO solution of ciprofloxacin (CP), or a derivative thereof, and an additional 0.12 equivalents of DBTL was added. The reaction continued to stir at 65° C. for four hours and then stirred at ambient temperature (20-25° C.) for 17 hours. Methanol was then added to the reaction and the addition of solvents allows the precipitation of the pharmaceutically-active polymer from the reaction mixture. The polymer was redissolved in solvent and again precipitated using solvents. The dissolution/precipitation cycle was repeated two additional times to afford the desired polymer. Variation of each reagent affords the different graftable polymers of the invention.

Polymers (17), (18), (19), and (20), which include ciprofloxacin as the biologically active agent, are depicted in Scheme 6 and were prepared according to this procedure. Tables 2 and 3 show additional examples of pharmaceutically active polymers including activated silicon grafting moieties that are prepared according to this procedure and by varying reagent amounts as listed in the table.

Figure 2:
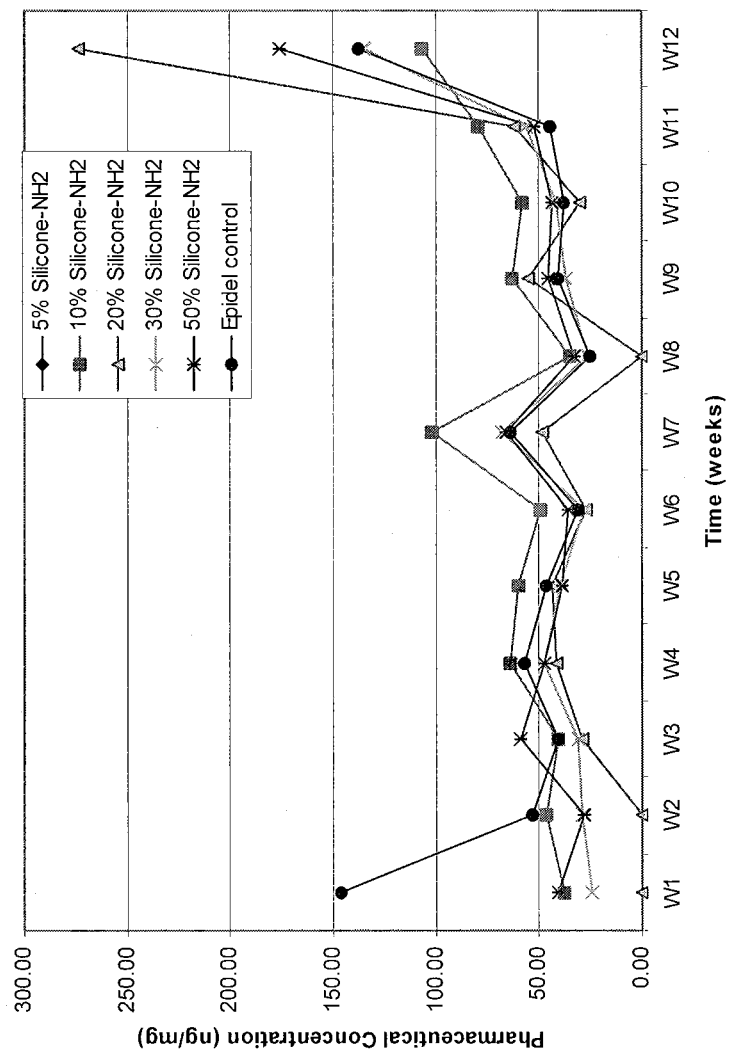
FIG. 2 shows the release of Ciprofloxacin as measured by HPLC by Polymer 17.
Figure 3:
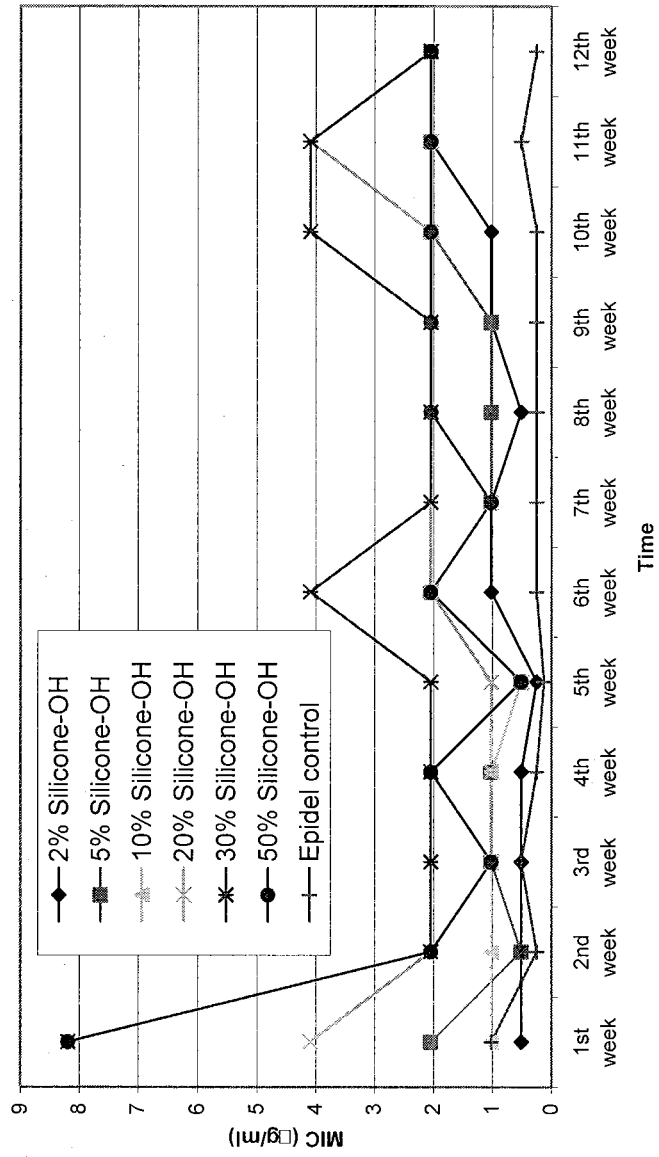
FIG. 3 shows the minimum inhibitory concentration (MIC) measured against an *E. coli* clinical strain for pharmaceutical released from Polymer 19 (depicted in Scheme 5 and as prepared in Example 5).
Figure 4:
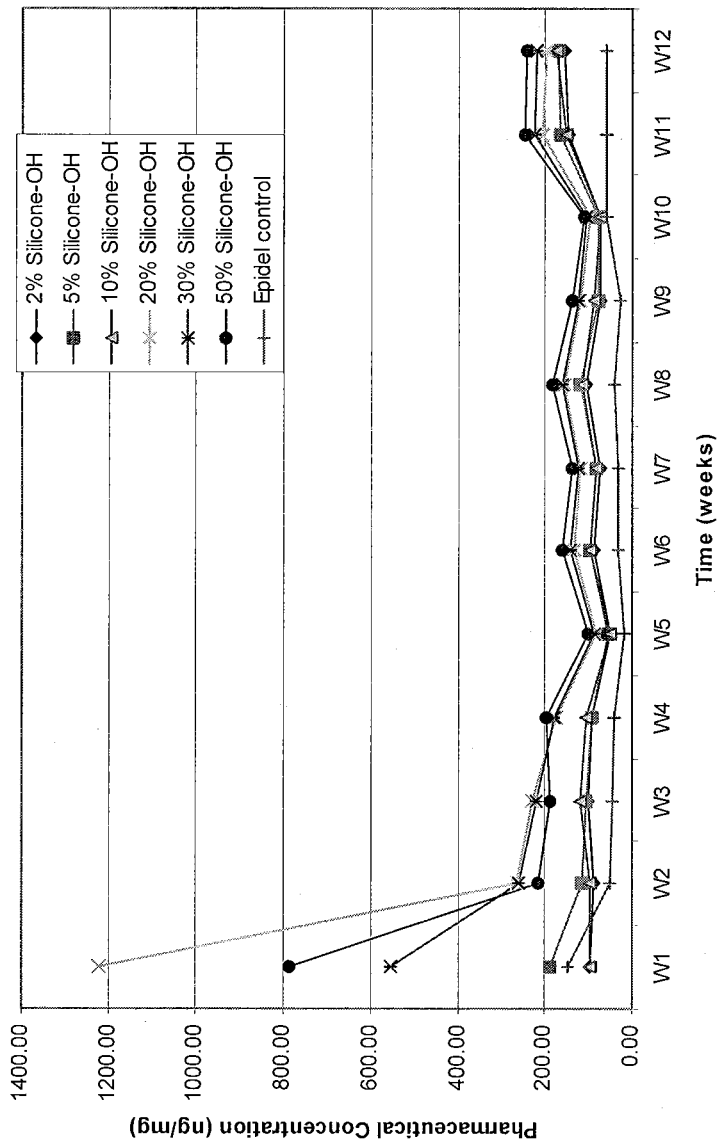
FIG. 4 shows the release of Ciprofloxacin as measured by HPLC by Polymer 19.

The drug-releasing properties of these polymers may be measured using the Minimum Inhibitory Concentration (MIC) assay or by using HPLC. FIG. 1 shows that polymers (17), which include from 5-50 w/w % activated silicon grafting moieties, are effective against *E. coli* over a twelve week period. FIG. 2 shows that these same polymers effectively release ciprofloxacin over a twelve week time frame. FIGS. 3 and 4 show MIC and HPLC data, respectively, for polymers (19). The data demonstrate that these polymers also effectively release ciprofloxacin, as measured over 12 weeks.

TABLE 2

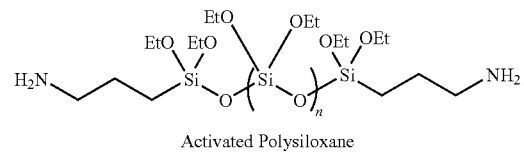

Activated Polysiloxane (2)

| Polymer | % w/w polysilicone/PCL | Pre-polymerization (1.5 h at 65° C.) | Polymerization (4 h at 65° C.; 17 h at 23° C.) | Mol. Wt./$T_m$ |
|---|---|---|---|---|
| 18a | 2 | Siloxane/PCL = 2.0 eq. THDI = 3.1 eq. DBTL = 0.2 eq. | CP = 1.0 eq. DBTL = 0.12 eq. | M.W. = 29.3 kg/mol Melt Temp. = 50.56° C. |
| 18b | 5 | Siloxane/PCL = 2.0 eq. THDI = 3.1 eq. DBTL = 0.2 eq. | CP = 1.0 eq. DBTL = 0.12 eq. | M.W. = 26.9 kg/mol Melt Temp. = 50.46° C. |
| 18c | 20 | Siloxane/PCL = 2.0 eq. THDI = 3.1 eq. DBTL = 0.2 eq. | CP = 1.0 eq. DBTL = 0.12 eq. | M.W. = 27.1 kg/mol Melt Temp. = 50.06° C. |
| 18d | 30 | Siloxane/PCL = 2.0 eq. THDI = 3.1 eq. DBTL = 0.2 eq. | CP = 1.0 eq. DBTL = 0.12 eq. | M.W. = 19.9 kg/mol Melt Temp. = 55.21° C. |
| 18e | 50 | Siloxane/PCL = 2.0 eq. THDI = 3.1 eq. DBTL = 0.2 eq. | CP = 1.0 eq. DBTL = 0.12 eq. | M.W. = 14.7 kg/mol Melt Temp. = 55.23° C. |

TABLE 3

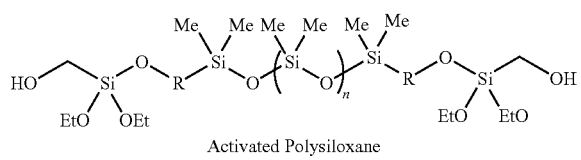

Activated Polysiloxane (4)

| Polymer | % w/w polysilicone/PCL | Pre-polymerization (1.5 h at 65° C.) | Polymerization (4 h at 65° C.; 17 h at 23° C.) | Mol. Wt./$T_m$ |
|---|---|---|---|---|
| 20a | 2 | Siloxane/PCL = 2.0 eq. THDI = 3.1 eq. DBTL = 0.2 eq. | CP = 1.0 eq. DBTL = 0.12 eq. | M.W. = 33.22 kg/mol Melt Temp. = 46.65° C. |

TABLE 3-continued

Activated Polysiloxane (4)

| Polymer | % w/w polysilicone/PCL | Pre-polymerization (1.5 h at 65° C.) | Polymerization (4 h at 65° C.; 17 h at 23° C.) | Mol. Wt./$T_m$ |
|---|---|---|---|---|
| 20b | 5 | Siloxane/PCL = 2.0 eq. THDI = 3.1 eq. DBTL = 0.2 eq. | CP = 1.0 eq. DBTL = 0.12 eq. | M.W. = 28.23 kg/mol Melt Temp. = 49.59° C. |
| 20c | 10 | Siloxane/PCL = 2.0 eq. THDI = 3.1 eq. DBTL = 0.2 eq. | CP = 1.0 eq. DBTL = 0.12 eq. | M.W. = 27.22 kg/mol Melt Temp. = 46.40° C. |
| 20d | 20 | Siloxane/PCL = 2.0 eq. THDI = 3.1 eq. DBTL = 0.2 eq. | CP = 1.0 eq. DBTL = 0.12 eq. | M.W. = 31.83 kg/mol Melt Temp. = 44.06° C. |
| 20e | 30 | Siloxane/PCL = 2.0 eq. THDI = 3.1 eq. DBTL = 0.2 eq. | CP = 1.0 eq. DBTL = 0.12 eq. | M.W. = 24.78 kg/mol Melt Temp. = 45.05° C. |
| 20f | 50 | Siloxane/PCL = 2.0 eq. THDI = 3.1 eq. DBTL = 0.2 eq. | CP = 1.0 eq. DBTL = 0.12 eq. | M.W. = 20.22 kg/mol Melt Temp. = 45.40° C. |

Example 6

Synthesis of Graftable, Pharmaceutically Active Polymers Including Hydridosilane Grafting Moieties Pharmaceutically active polymers including polyurethane segments and hydridosilane grafting moieties are prepared by prepolymerizing a mixture of the selected hydridosilane monomer (e.g. compound (5)) with a diisocyanate in the presence of a catalyst. Other compounds such as PCL can be included in the prepolymerization. In the second stage of polymerization, the pharmaceutically-active component and any additional catalyst are added to afford the desired pharmaceutically active polymers.

Example 7

Synthesis of Graftable, Pharmaceutically Active Polymers Including UV-Labile Grafting Moieties

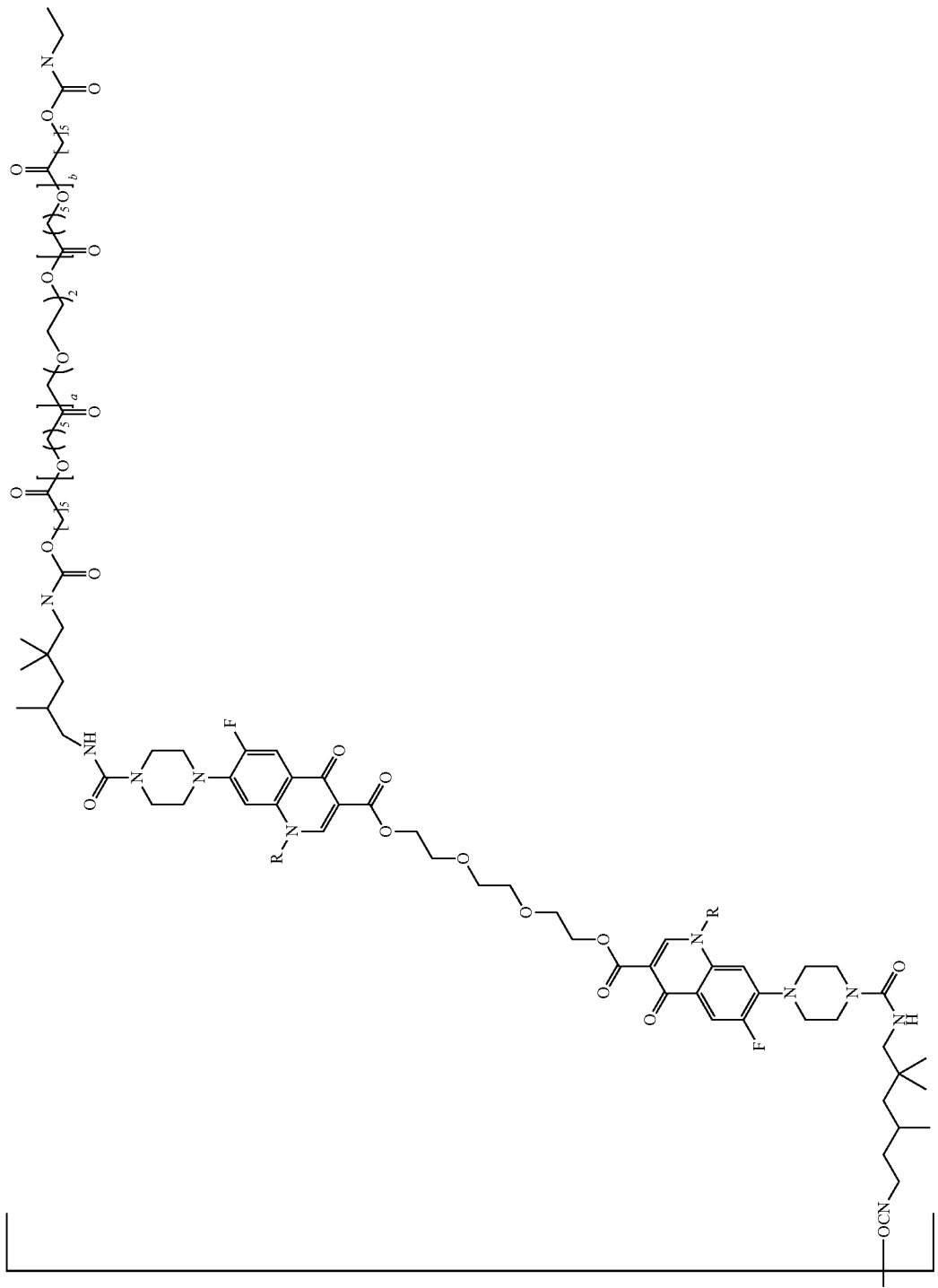

-continued
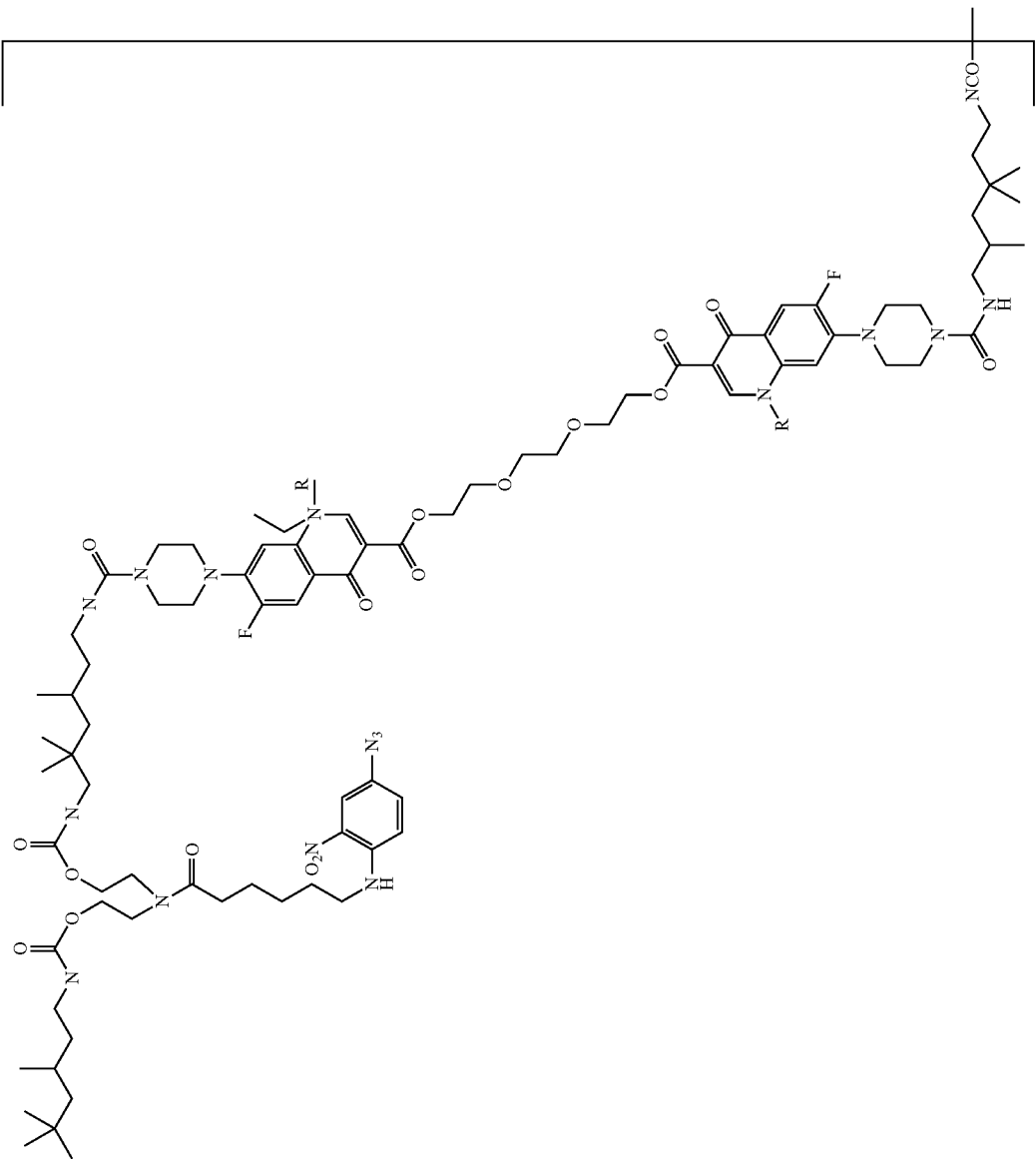

Pharmaceutically active polymers including polyurethane segments and UV-labile grafting moieties were prepared by prepolymerizing a mixture of the selected UV-labile monomer (e.g. compound (6) or compound (7)) with a diisocyanate in the presence of a catalyst. Reagent A (also referred to as "SANPAH") is another UV-labile monomer that is useful in the polymers and articles of the invention. Other compounds such as PCL may be optionally included in the prepolymerization. In the second stage of polymerization, the pharmaceutically-active component and any additional catalyst were added to afford the desired pharmaceutically active polymers.

Scheme 7 shows Polymer (21) which includes ciprofloxacin as the biologically active agent and is prepared according to this procedure. Table 4 shows additional examples of pharmaceutically active polymers including UV-labile grafting moieties that are prepared according to this procedure.

TABLE 4

| Polymer | Prepolymerization | Polymerization Stage | Molecular Weight | Melt Temp. |
| --- | --- | --- | --- | --- |
| 21a | PCL = 2.0 equiv.<br>THDI = 3.2 equiv.<br>DBTL = 0.2 equiv.<br>Reagent A = 0.02 equiv.<br>1.5 hours 65° C. | CP$_2$TEG = 1.0 equiv.<br>DBTL = 0.12 equiv.<br>4 hrs 65° C., 17 hrs R.T. | 33.21 kg/mol | 44.12° C. |
| 21b | PCL = 2.0 equiv.<br>THDI = 3.2 equiv.<br>DBTL = 0.2 equiv.<br>Reagent A = 0.05 equiv.<br>1.5 hours 65° C. | CP$_2$TEG = 1.0 equiv.<br>DBTL = 0.12 equiv.<br>4 hrs 65° C., 17 hrs R.T. | 37.49 kg/mol | 34.86° C. |
| 21c | PCL = 2.0 equiv.<br>THDI = 3.2 equiv.<br>DBTL = 0.2 equiv.<br>Reagent A = 0.1 equiv.<br>1.5 hours 65° C. | CP$_2$TEG = 1.0 equiv.<br>DBTL = 0.12 equiv.<br>4 hrs 65° C., 17 hrs R.T. | 38.04 kg/mol | 44.48° C. |
| 21d | PCL = 2.0 equiv.<br>THDI = 3.2 equiv.<br>DBTL = 0.2 equiv.<br>Reagent A = 0.2 equiv.<br>1.5 hours 65° C. | CP$_2$TEG = 1.0 equiv.<br>DBTL = 0.12 equiv.<br>4 hrs 65° C., 17 hrs R.T. | 33.59 kg/mol | 36.25° C. |

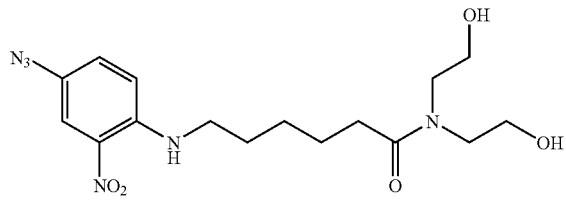

Reagent A (SANPAH): photo-active component

Example 8

Synthesis of Graftable, Pharmaceutically Active Polymers Including Chlorhexidine and Activated Silicon Grafting Moieties Scheme 8
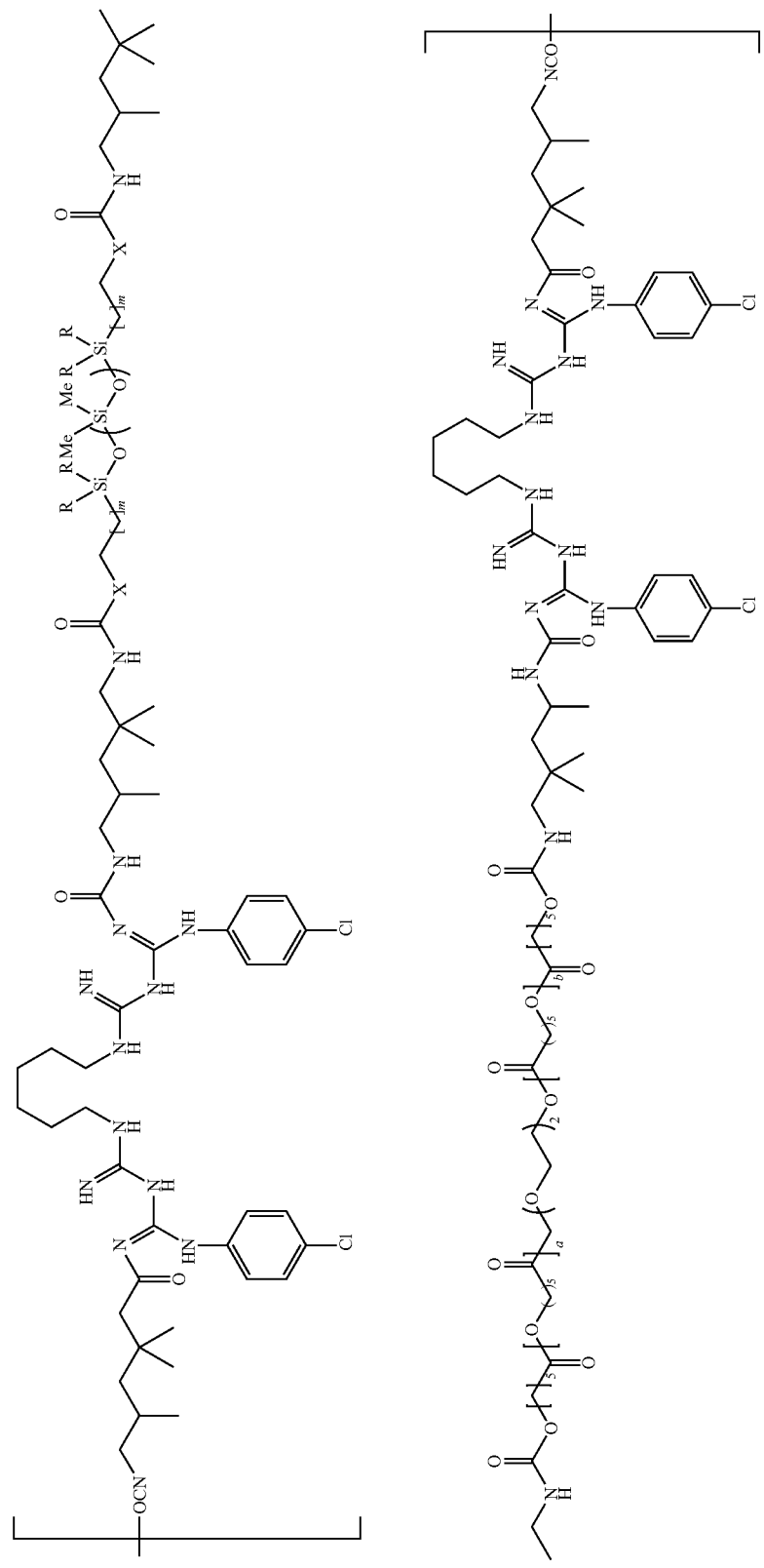
22 X = NH, R = Me
23 X = NH, R = OEt Graftable pharmaceutically active polymers that include chlorhexidine as the biologically active agent are prepared in a manner analogous to the ciprofloxacin-containing polymers of Example 5. The synthesis of chlorhexidine-containing polymers is described below. Scheme 8 depicts graftable polymers 22 and 23, each of which includes chlorhexidine.

A mixture of 10% (w/w) compound (2) in PCL (2.0 equivalents relative to CH), THDI (3.1 equivalents), and dibutyltin dilaurate (DBTL; 0.2 equivalents) was heated in dimethylsulfoxide (DMSO) at 65° C. for 1.5 hours. At that time, a DMSO solution of chlorhexidine (CH), or derivatives thereof, and an additional 0.12 equivalents of DBTL was added. The reaction continued to stir at 65° C. for four hours and then stirred at ambient temperature (20-25° C.) for 17 hours. Methanol was then added to the reaction and the addition of solvents allows the precipitation of the pharmaceutically-active polymer from the reaction mixture. The polymer was redissolved in solvent and again precipitated using solvents. The dissolution/precipitation cycle was repeated two additional times to afford the desired polymer. Variation of each reagent affords the different graftable polymers of the invention. Table 5 shows additional data for polymers 22 and 23.

The drug-releasing properties of these polymers may be measured using the Minimum Inhibitory Concentration (MIC) assay or by using HPLC.

TABLE 5

| Polymer | Prepolymerization | Polymerization Stage | Molecular Weight | Melt Temp. |
|---------|-------------------|----------------------|------------------|------------|
| 22 | PCL = 2.0 THDI = 3.1; DBTL = 0.2 1.5 hours 65° C. | Chlorhexidine = 1.0 DBTL = 0.12 4 hrs 65° C., 17 hrs R.T. | 22.86 kg/mol | 49.27° C. |
| 23 | PCL = 2.0 equiv. THDI = 3.1 equiv. DBTL = 0.2 equiv. Reagent A = 0.02 equiv. 1.5 hours 65° C. | Chlorhexidine = 1.0 DBTL = 0.12 4 hrs 65° C., 17 hrs R.T. | 24.21 kg/mol | 50.35° C. |

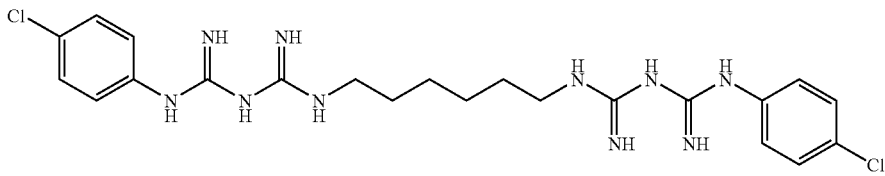

Chlorhexidine

Example 9

Synthesis of Graftable, Pharmaceutically Active Polymers Including Chlorhexidine and UV-Labile Grafting Moieties Scheme 9
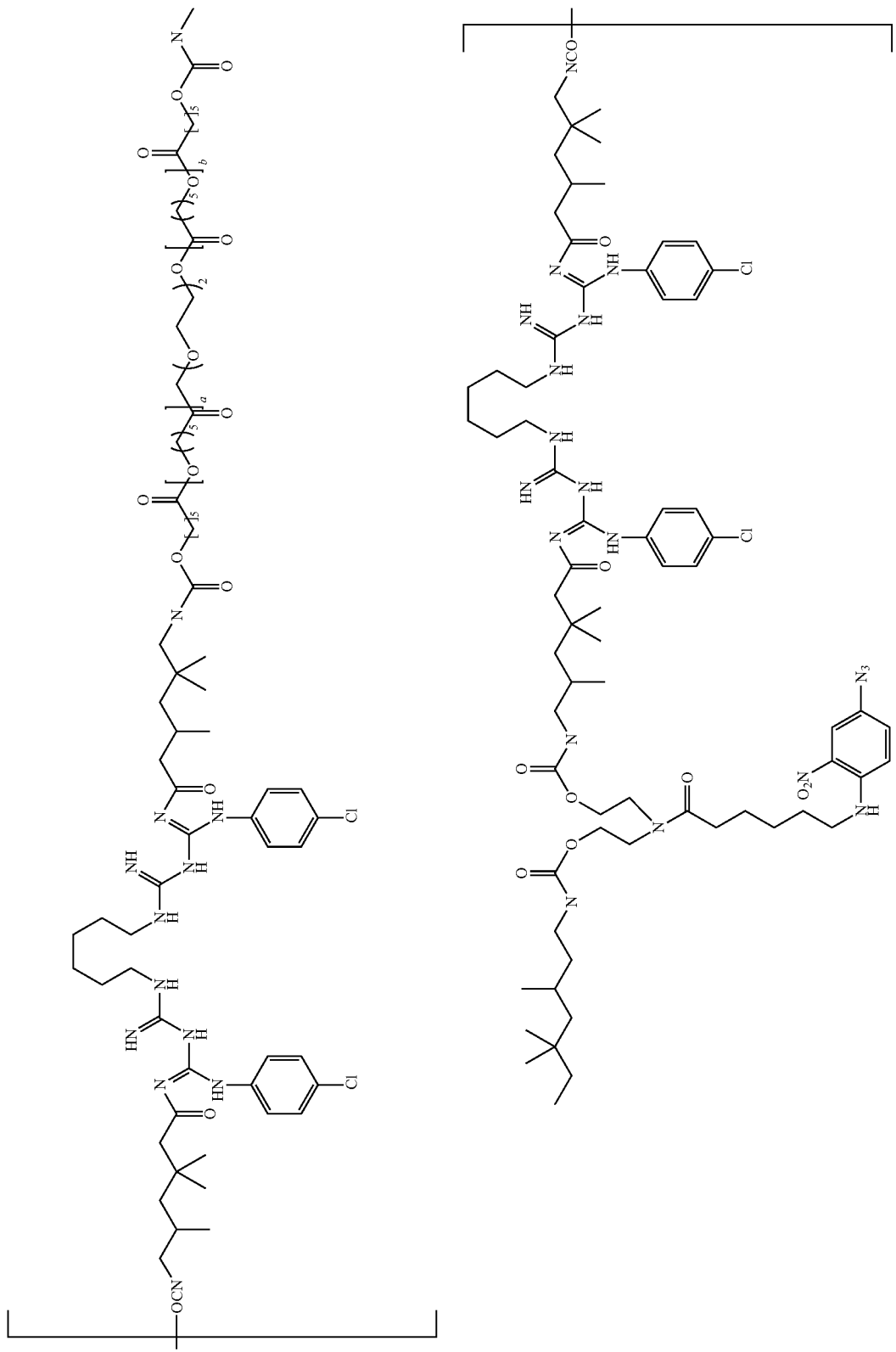

Pharmaceutically active polymers including chlorhexidine, polyurethane segments and UV-labile grafting moieties can be prepared in a manner analogous to Example 7. Scheme 9 depicts a chlorhexidine-containing graftable polymer (24) and the synthesis of this polymer is further described below. Table 6 provides additional data for Polymer 24(a)

A mixture of 2% (w/w) Reagent A in PCL (2.0 equivalents relative to CH), THDI (3.1 equivalents), and dibutyltin dilaurate (DBTL; 0.2 equivalents) was heated in dimethylsulfoxide (DMSO) at 65° C. for 1.5 hours. At that time, a DMSO solution of chlorhexidine (CH) and an additional 0.12 equivalents of DBTL was added. The reaction continued to stir at 65° C. for four hours and then stirred at ambient temperature (20-25° C.) for 17 hours. Methanol was then added to the reaction and the addition of solvents allows the precipitation of the pharmaceutically-active polymer from the reaction mixture. The polymer was redissolved in solvent and again precipitated using solvents. The dissolution/precipitation cycle was repeated two additional times to afford the desired polymer. Variation of each reagent affords the different graftable polymers of the invention.

TABLE 6

| Polymer | Prepolymerization | Polymerization Stage | Molecular Weight | Melt Temp. |
|---|---|---|---|---|
| 24a | PCL = 2.0 THDI = 3.1; DBTL = 0.2 1.5 hours 65° C. | Chlorhexidine = 1.0 DBTL = 0.12 4 hrs 65° C., 17 hrs R.T. | 22.86 kg/mol | 49.27° C. |

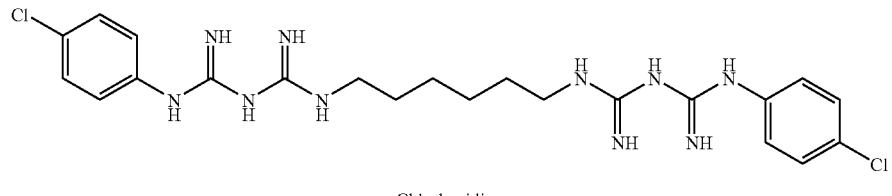

Chlorhexidine

Example 10

Procedure for Grafting a Graftable, Pharmaceutically Active Polymer Including Activated Polysiloxane Grafting Moieties to a Polysilicone Polymer A graftable polymer including an activated silicon grafting moiety, such as polymers (17)-(20) and other polymers prepared according to Example 5, was grafted to the surface of base polymer such as polysilicone according to the following procedure. A polysilicone surface was treated with 10M aqueous NaOH for 2 hours at ambient temperature. The silicone surface was then washed twice with deionized water (e.g. water obtained after purification through a Millipore system, hereafter referred to as Milli-Q water) and then dried in an oven at 120° C. for two hours. A solution of the graftable polymer in THF was prepared and dipping of the polysilicone surface into this solution allowed for coating of the surface. This procedure was repeated in order to achieve the desired coating thickness. Once the desired coating thickness was achieved, the grafted polymer was allowed to cure for a minimum of 16 hours at ambient temperature and under conditions of 10-50% relative humidity.

Figure 5:
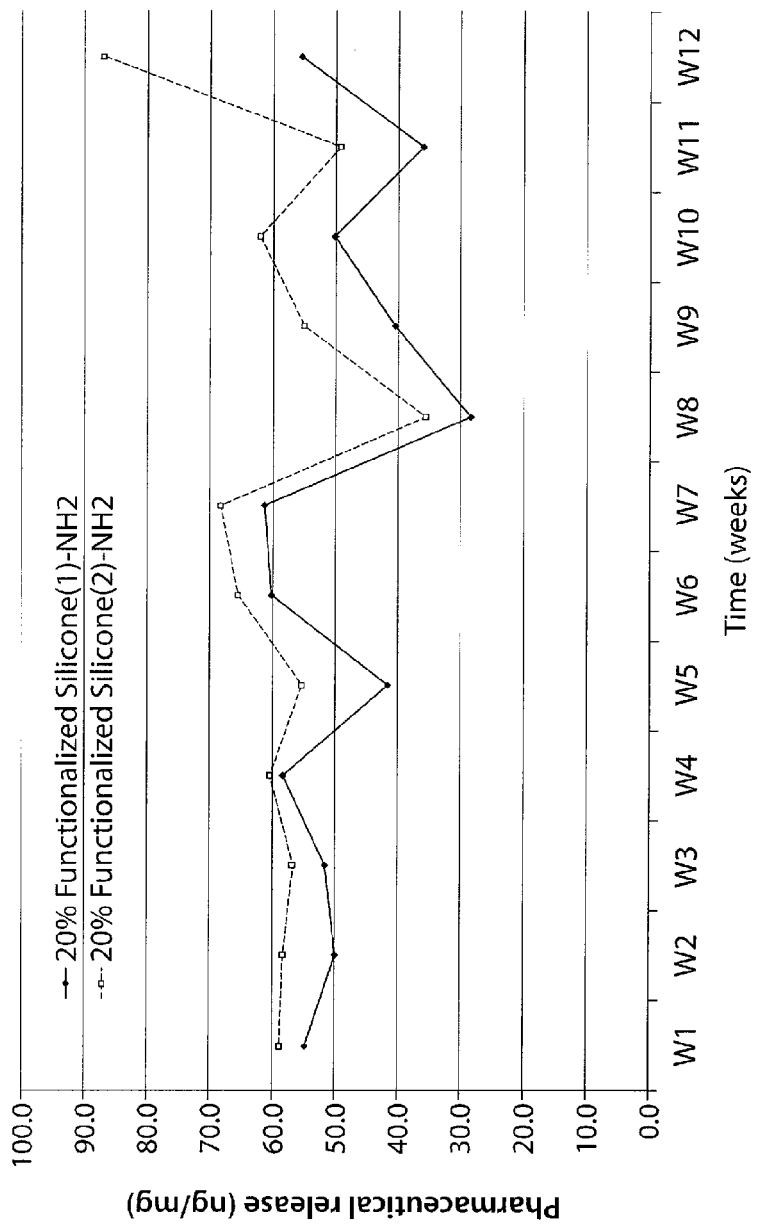
FIG. 5 shows the minimum inhibitory concentration (MIC) measured against an *E. coli* clinical strain for pharmaceutical released from Polymer 18 (depicted in Scheme 5 and as prepared in Example 5) grafted onto a silicone surface according to Example 10.

FIG. 5 shows drug release by polymer (18), containing 20% w/w activated silicone grafting moieties, grafted to silicone tubing. The data show that the grafted polymer is effective at releasing drugs as measured over a twelve week period.

Example 11

Procedure for Grafting a Graftable, Pharmaceutically Active Polymer Including Activated Polysiloxane Grafting Moieties to a Polysilicone Polymer Using Acetoxysilane Additives A graftable polymer including an activated silicon grafting moiety, such as polymers (17)-(20) and other polymers prepared according to Example 5, was grafted to the surface of base polymer such as polysilicone according to the following procedure and incorporates the use of acetoxysilane additives. A polysilicone surface was treated with 10M aqueous NaOH for 2 hours at ambient temperature. The silicone surface was then washed twice with deionized water (e.g. water obtained after purification through a Millipore system, hereafter referred to as Milli-Q water) and then dried in an oven at 120° C. for two hours. A solution of graftable polymer is THF was prepared as described in Example 8. A second solution of the graftable polymer and acetoxysilane additives in THF was also prepared by combining 70 g of methyltriacetoxysilane, 70 g of ethyltriacetoxysilane, 5 g of the graftable polymer, and 1 g of acetic acid in 100 mL THF. Other mixtures and ratios of alkoxy- or acetoxysilane reagents may be used.

The first solution was then mixed with the second solution in a 10:1 (v/v) ratio to yield a mixed solution. The polysilicone surface was then dipped into this mixed solution and the resulting coated polysilicone surface was dried under ambient conditions. This procedure was repeated multiple times in order to achieve the desired coating thickness. Once the desired coating thickness was achieved, the grafted polymer was allowed to cure for a minimum of 16 hours at ambient temperature and under conditions of 10-50% relative humidity.

Figure 6:
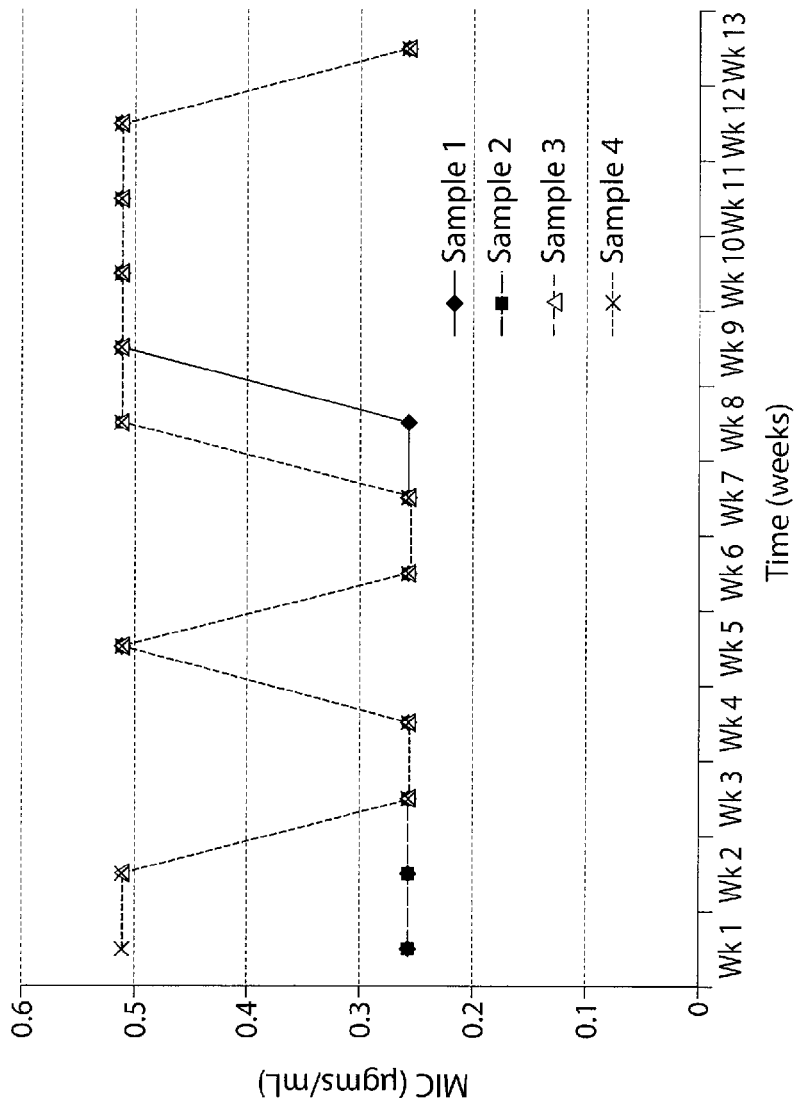
FIG. 6 shows the minimum inhibitory concentration (MIC) measured against an *E. coli* clinical strain for Polymer 18 grafted to a silicone surface using triacetoxymethylsilane as a tie-coat according to the procedure of Example 11.

FIG. 6 shows MIC data for polymer (18) grafted to silicone tubing using triacetoxymethylsilane. These grafted polymers remain effective against *E. coli* as measured over a thirteen week period.

Example 12

Procedure for Grafting a Pharmaceutically Active Polymer Including Hydridosilane Grafting Moieties to a Latex Polymer A graftable polymer including a hydridosilane grafting moiety, such as those prepared in Example 6, was grafted to the surface of a base polymer, such as latex, according to the following procedure. A solution of the graftable polymer and a Pt-containing catalyst (e.g. chloroplatinic acid or Karstedt's catalyst) in THF was prepared. A latex surface was then dipped into the solution to coat the surface and then dried completely under ambient conditions.

Example 13

Procedure for Grafting a Pharmaceutically Active Polymer Including UV Labile Grafting Moieties to a Base Polymer A graftable polymer that includes a UV labile grafting moiety, such as polymer (21) and other polymers prepared according to Example 7, was grafted to the surface of a base polymer such as silicone, polyethylene, polyvinylchloride, or polyurethane according to the following procedure. A solution of the graftable polymer in THF was prepared. A base polymer surface was then dipped into the solution to coat the surface and dried completely under ambient conditions. The coated polymer was then irradiated under inert atmosphere (e.g. Ar or $N_2$ atmosphere) using a light source that provides wavelengths between 300-460 nm. The grafted polymer was cured for 16 hours under ambient conditions.

Figure 7:
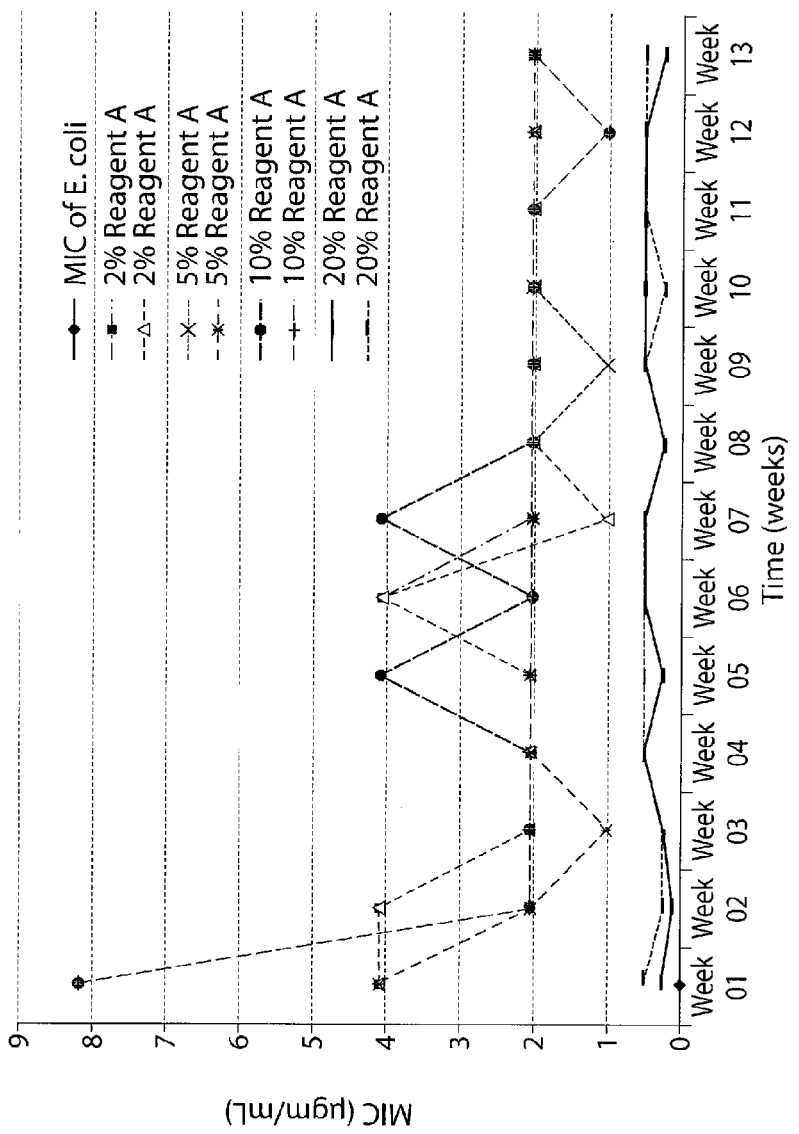
FIG. 7 shows the minimum inhibitory concentration (MIC) measured against an *E. coli* clinical strain for pharmaceutical released from Polymer 21 (depicted in Scheme 6 and as prepared in Example 7) grafted onto a polyurethane surface according to the procedure of Example 13.

FIG. 7 shows MIC data for polymers (21) grafted to a polyurethane surface. The polymer can contain from 2%-20% (w/w) of the UV labile grafting moiety. The graph shows that the grafted polymers are effective against *E. Coli* over a thirteen week period and that polymers that include a higher percentage of grafting moieties have lower MIC values.

FIG. 8 shows MIC data for polymers (21) grafted to polyvinylchloride (PVC). These grafted polymers remain active against *E. coli* as measured over a time period that exceeds 90 days.

FIG. 9 shows that polymers (21) grafted to polyurethanes or to silicone can continue to release ciprofloxacin over a twelve week period.

Example 14

Preparation of Grafted Articles Useful in Combination Therapies-Grafting to Silicone Surfaces A mixture of a graftable polymer that includes an activated silicon grafting moiety and ciprofloxacin as the biologically active agent (e.g., a polymer prepared according to Example 5) and a second graftable polymer that includes an activated silicon grafting moiety and chlorhexidine as the biologically active agent (e.g., a polymer prepared according to Example 8) can be grafted to the surface of base polymer such as polysilicone according to the following procedure. A polysilicone surface can be treated with 10M aqueous NaOH for 2 hours at ambient temperature. The silicone surface can then be washed twice with Milli-Q water and dry in an oven at 120° C. for two hours. A solution of the two different graftable polymers in THF can then be prepared. Dipping of the polysilicone surface into this solution can allow for coating of the surface. This procedure can be repeated in order to achieve the desired coating thickness. Once the desired coating thickness is achieved, the grafted polymer can then cure for a minimum of 16 hours at ambient temperature and under conditions of 10-50% relative humidity. This procedure can afford the desired grafted article.

Example 15

Procedure for Grafting a Pharmaceutically Active Polymer Including UV Labile Grafting Moieties to a Base Polymer A mixture of a graftable polymer that includes a UV labile grafting moiety and ciprofloxacin as the biologically active agent (e.g., a polymer prepared according to Example 7) and a second graftable polymer that includes a UV labile grafting moiety and chlorhexidine as the biologically active agent (e.g., a polymer prepared according to Example 9) can be grafted to the surface of a base polymer such as silicone, polyethylene, polyvinylchloride, or polyurethane according to the following procedure. A solution of the two different graftable polymers in THF can then be prepared. A base polymer surface can then be dipped into the solution to coat the surface and can then be dried completely under ambient conditions. The coated polymer can then be irradiated under inert atmosphere (e.g. Ar or $N_2$ atmosphere) using a light source that provides wavelengths between 300-460 nm. The grafted polymer can then cure for 16 hours under ambient conditions. This procedure can then afford the grafted article.

Example 16

Grafting of a Pharmaceutically Active Polymer Including an Activated Polysiloxane Moiety to a Ceramic Surface A graftable polymer including an activated polysiloxane grafting moiety, such as those prepared in Example 5, may be grafted to the surface of a ceramic base such as $TiO_2$ using a procedure such as that described in U.S. Pat. No. 6,033,781. A solution including the graftable polymer in an organic solvent such as THF or ethanol may be added to a solution of the $TiO_2$ and alkoxide base. The reaction may be allowed to stir for 2-16 hours and the coated $TiO_2$ may then be dried under inert atmosphere conditions. The process may be repeated until the desired coating thickness is achieved.

Example 17

Grafting of a Pharmaceutically Active Polymer Including UV-Labile Grafting Moieties to a Metal Surface A graftable polymer including a UV labile grafting moiety, such as those prepared in Example 7, can be grafted to a metal surface, such as stainless steel, using photolytic activation. A solution of the graftable polymer in THF can be prepared. A metal surface can then be dipped into the solution to coat the surface and then dried completely under ambient conditions. The coated polymer can then be irradiated under inert atmosphere (e.g. Ar or $N_2$ atmosphere) using a light source that provides wavelengths between 300-460 nm. The grafted polymer can then be cured for 16 hours under ambient conditions.

Example 18

Grafting of a Pharmaceutically Active Polymer Including UV-Labile Grafting Moieties to a Metal Surface Using Thermolytic Activation The polymers prepared in Example 7 include azide-containing grafting moieties that may also be grafted to a surface

61 under thermolytic activation. These polymers can be grafted to a metal surface, such as stainless steel, according to procedures such as that described in U.S. Pat. No. 3,666,536, herein incorporated by reference. A solution of the graftable polymer in THF can be prepared. A metal surface can then be dipped into the solution to coat the surface and can then be dried completely under ambient conditions. The coated polymer can then be heated under inert atmosphere (e.g. Ar or $N_2$ atmosphere) at temperatures that range between 300-500° C. The grafted polymer can then be cured for 16 hours under ambient conditions.

Example 19

Grafting of Pharmaceutically Active Polymers Including UV-Labile Grafting Moieties to Base Polymers Using Tie Coats A graftable polymer, such as those prepared in Example 7, was grafted to the surface of a base polymer, such as silicone, according to the following procedure. A 1:2 (Solution A) and 1:2 (Solution B) weight percent solution of the graftable polymer and tie coat in THF was prepared. The polysilicone surface was then dipped into Solution A first, and the resulting coated polysilicone surface was then dried under ambient conditions. The resulting treated surface was then dipped into the second Solution B and dried under ambient conditions. The second dipping procedure using Solution B can be repeated multiple times in order to achieve the desired coating thickness. Once the desired coating thickness was achieved, the grafted polymer was allowed to cure for a minimum of 16 hours at ambient temperature and under conditions of 10-50% relative humidity.

In this procedure, the graftable polymer:tie coat ratios were varied. For example, a 1:2 and 1:1 weight percent solution of the graftable polymer and tie coat in THF were used, respectively for Solutions A and B. Alternatively, a single weight percent solution (e.g., 1:1) was used for each dipping procedure. The effect of varying the polymer:tie coat ratio can be seen in FIG. 10. In this figure, "Epidel 1" refers to silicone tubing coated with a 2:1 w/w formulation of polymer:tie coat and "Epidel 2" refers to silicone tubing coated with a 1:2 w/w formulation of polymer:tie coat. These coated articles are challenged with *Staphylococcus aureus*, and the results thus obtained are compared to results using uncoated silicone tubing and silver coated tubing. Both Epidels 1 and 2 are more effective against *S. aureus* than uncoated or silver coated tubing, and it can be seen that the decrease in *S. aureus* counts occurs more rapidly using Epidel 1 compared to Epidel 2. Without being bound by theory, it is thought that increasing the amount of tie-coat used leads to decreased amounts of pharmaceutically active polymer on the surface, thereby affecting rates of hydrolysis and relase of the pharmaceutically active agent (in this case, ciprofloxacin). The application of a tie-coat layer separately from a graftable polymer layer versus the coating of an article with an admixture of tie-coat and polymer can similarly affect the amount of pharmaceutically active polymer present on the surface of a coated article, with a greater amount of pharmaceutically active polymer present using the former approach.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A graftable polymer having the following structure:

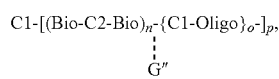

wherein (i) each Bio is, independently, one or more biologically active agents or precursors thereof;

(ii) C1 is a coupling segment (iii) C2 is a hydrolysable coupling segment or a polyamide linker susceptible to hydrolysis by a peptidase enzyme linking Bio to Bio;

(iv) Oligo comprises a repeating monomeric unit or units that number less than 50 monomeric units and has a molecular weight less than 5 KDa;

(v) G" is a grafting moiety that has the following structure:

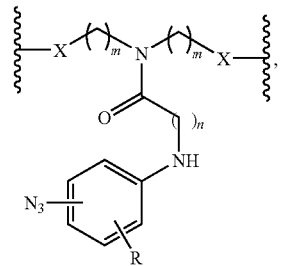

wherein, independently, a. X is either —NH— or —O—;

b. m is an integer between 1 and 6;

c. n is an integer between 0 and 6; and d. R is an optional substituent selected from —H; —NO$_2$, or —CF$_3$;

wherein each of n, o, and p is independently an integer greater than 0, and wherein G" is covalently tethered to Bio, C1, C2, or Oligo.

2. The graftable polymer of claim 1, wherein Bio comprises ciprofloxacin and/or chlorhexidine.

3. The graftable polymer of claim 1, wherein G″ is

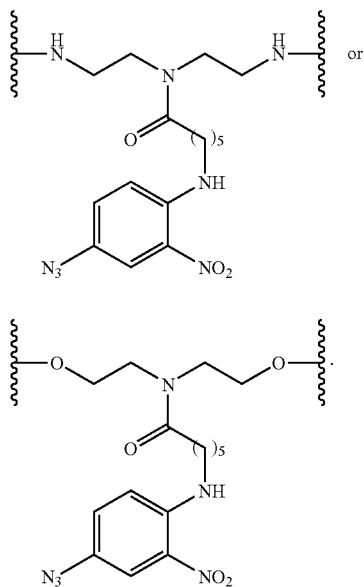

4. The graftable polymer of claim 3, wherein
Bio is ciprofloxacin or chlorhexidine;
C1 comprises 2,2,4-trimethylhexamethylene diisocyanate (THDI);
Oligo comprises poly(ε-caprolactone) diol (PCL); and G″ is 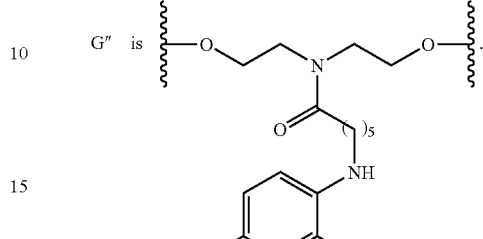.

5. The graftable polymer of claim 1, wherein said graftable moiety requires photolytic or thermolytic activation for grafting to a polymer surface.

* * * * *